US012599663B2

(12) United States Patent
Jackson et al.

(10) Patent No.: US 12,599,663 B2
(45) Date of Patent: Apr. 14, 2026

(54) MULTIVALENT PEPTIDE CONJUGATES FOR SUSTAINED INTRA-ARTICULAR TREATMENT OF JOINT INFLAMMATION

(71) Applicant: Valitor, Inc., Berkeley, CA (US)

(72) Inventors: Wesley M. Jackson, Berkeley, CA (US); Mavish Mahomed, Berkeley, CA (US); Livia W. Brier, Berkeley, CA (US); Kevin E. Healy, Berkeley, CA (US)

(73) Assignee: VALITOR, INC., Berkeley, CA (US)

( * ) Notice: Subject to any disclaimer, the term of this patent is extended or adjusted under 35 U.S.C. 154(b) by 1135 days.

(21) Appl. No.: 16/977,636

(22) PCT Filed: Mar. 8, 2019

(86) PCT No.: PCT/US2019/021460
§ 371 (c)(1),
(2) Date: Sep. 2, 2020

(87) PCT Pub. No.: WO2019/173777
PCT Pub. Date: Sep. 12, 2019

(65) Prior Publication Data
US 2021/0046181 A1      Feb. 18, 2021

Related U.S. Application Data

(60) Provisional application No. 62/640,749, filed on Mar. 9, 2018.

(51) Int. Cl.
| A61K 47/61 | (2017.01) |
| A61K 31/728 | (2006.01) |
| A61K 39/395 | (2006.01) |
| A61K 47/22 | (2006.01) |
| A61K 47/68 | (2017.01) |
| A61P 19/02 | (2006.01) |

(52) U.S. Cl.
CPC ........ *A61K 39/3955* (2013.01); *A61K 31/728* (2013.01); *A61K 47/22* (2013.01); *A61K 47/61* (2017.08); *A61K 47/68* (2017.08); *A61P 19/02* (2018.01)

(58) Field of Classification Search
CPC .. A61K 39/3955; A61K 31/728; A61K 47/22; A61K 47/61; A61K 47/68; A61K 2039/505; A61K 9/0024; A61K 38/00; A61K 9/0019; A61K 2039/54; A61K 2039/545; A61P 19/02; C07K 2317/92; C07K 2317/94; C07K 16/241; C07K 16/245; A61L 27/20; A61L 27/50; A61L 27/54; A61L 2300/256; A61L 2300/426; A61L 2300/252; A61L 2300/432; A61L 2400/06; C08L 5/08
See application file for complete search history.

(56) References Cited

U.S. PATENT DOCUMENTS

| 5,162,218 | A | 11/1992 | Schultz |
| 6,781,030 | B1 | 8/2004 | Baguisi et al. |
| 6,964,859 | B2 | 11/2005 | Rajbhandary et al. |
| 7,122,636 | B1 | 10/2006 | Hsei et al. |
| 8,591,885 | B2 | 11/2013 | Chang et al. |
| 8,759,322 | B2 | 6/2014 | Akiyoshi et al. |
| 9,034,624 | B2 | 5/2015 | D'este et al. |
| 9,221,893 | B2 | 12/2015 | Hahn et al. |
| 9,428,561 | B2 | 8/2016 | Healy et al. |
| 9,925,237 | B2 | 3/2018 | Healy et al. |
| 10,350,267 | B2 | 7/2019 | Healy et al. |
| 10,653,621 | B2 | 5/2020 | Wu et al. |
| 10,765,759 | B2 | 9/2020 | Healy et al. |
| 10,899,828 | B2 | 1/2021 | Koenig et al. |
| 11,111,291 | B2 | 9/2021 | Famili et al. |
| 11,229,709 | B2 | 1/2022 | Hammond et al. |
| 11,291,707 | B2 | 4/2022 | Healy et al. |
| 11,723,982 | B2 | 8/2023 | Healy et al. |
| 2003/0003048 | A1 | 1/2003 | Li et al. |
| 2003/0236214 | A1 | 12/2003 | Wolff et al. |
| 2004/0038876 | A1 | 2/2004 | Pepinsky et al. |
| 2004/0116348 | A1 | 6/2004 | Chau et al. |
| 2005/0025752 | A1 | 2/2005 | Kutryk et al. |
| 2005/0260651 | A1 | 11/2005 | Calias et al. |
| 2005/0282747 | A1 | 12/2005 | Clark et al. |
| 2006/0094643 | A1 | 5/2006 | Svirkin et al. |
| 2006/0171920 | A1 | 8/2006 | Shechter et al. |
| 2006/0246523 | A1 | 11/2006 | Bieniarz et al. |
| 2007/0026518 | A1 | 2/2007 | Healy et al. |
| 2008/0113935 | A1 | 5/2008 | Yedgar et al. |
| 2008/0268051 | A1 | 10/2008 | Hughes et al. |
| 2010/0104585 | A1 | 4/2010 | Kiessling et al. |

(Continued)

FOREIGN PATENT DOCUMENTS

| WO | 0045848 A1 | 8/2000 |
| WO | 03031581 A2 | 4/2003 |

(Continued)

OTHER PUBLICATIONS

Westacott et al (Osteoarthritis and Cartilage, 2000, 8, 213-221) (Year: 2000).*
Ahmad et al (Osteoarthritis and Cartilage, 2009, 17, 1049-1055). (Year: 2009).*
Al-Muhammed et al., "In-vivo studies on dexamethasone sodium phosphate liposomes," J. Microencapsul., 13, pp. 293-306 (1996).
Chonn and Cullis, "Recent advances in liposomal drug-delivery systems," Curr. Opin. Biotechnol., 6, pp. 698-708 (1995).
Eyles et al., "Oral delivery and fate of poly(lactic acid) microsphere-encapsulated interferon in rats," J. Pharm. Pharmacol., 49, pp. 669-674 (1997).
Gao et al., "Controlled release of a contraceptive steroid from biodegradable and injectable gel formulations: in vitro evaluation," Pharm. Res., 12, pp. 857-863 (1995).

(Continued)

*Primary Examiner* — Sudhakar Katakam
(74) *Attorney, Agent, or Firm* — Mintz Levin Cohn Ferris Glovsky and Popeo, P.C.

(57) ABSTRACT

The present disclosure is directed to peptide-polymer conjugates, and to their use in treating intra-articular diseases or disorders.

23 Claims, 12 Drawing Sheets

Specification includes a Sequence Listing.

(56)                References Cited

U.S. PATENT DOCUMENTS

| | | | | |
|---|---|---|---|---|
| 2010/0210509 | A1 | 8/2010 | Oh et al. | |
| 2011/0046038 | A1* | 2/2011 | Healy | A61K 47/58 |
| | | | | 530/391.1 |
| 2011/0053865 | A1 | 3/2011 | Sauders | |
| 2011/0111035 | A1 | 5/2011 | Washburn et al. | |
| 2012/0014975 | A1 | 1/2012 | Hegan et al. | |
| 2012/0282211 | A1 | 11/2012 | Washburn et al. | |
| 2014/0038892 | A1* | 2/2014 | Yayon | A61K 38/363 |
| | | | | 530/382 |
| 2015/0030626 | A1 | 1/2015 | Pietersz et al. | |
| 2015/0110782 | A1* | 4/2015 | Silence | C07K 16/18 |
| | | | | 530/387.3 |
| 2016/0158270 | A1 | 6/2016 | Singh et al. | |
| 2017/0112899 | A1 | 4/2017 | Healy et al. | |
| 2018/0293360 | A1 | 10/2018 | Kelley et al. | |
| 2018/0318431 | A1 | 11/2018 | Healy et al. | |
| 2018/0325999 | A1 | 11/2018 | Healy et al. | |
| 2019/0142953 | A1 | 5/2019 | Edelman et al. | |
| 2020/0085910 | A1 | 3/2020 | Healy et al. | |
| 2020/0095340 | A1 | 3/2020 | Wesche et al. | |
| 2021/0113655 | A1 | 4/2021 | Healy et al. | |
| 2021/0113702 | A1 | 4/2021 | Healy et al. | |
| 2022/0251185 | A1 | 8/2022 | Jackson et al. | |
| 2022/0265763 | A1 | 8/2022 | Healy et al. | |
| 2024/0148882 | A1 | 5/2024 | Healy et al. | |

FOREIGN PATENT DOCUMENTS

| | | | | |
|---|---|---|---|---|
| WO | 2005054860 | A1 | 6/2005 | |
| WO | 2005110489 | A2 | 11/2005 | |
| WO | 2009120893 | A2 | 10/2009 | |
| WO | 2011039370 | | 7/2011 | |
| WO | 2012028716 | | 3/2012 | |
| WO | WO-2012140650 | A2 * | 10/2012 ........... A61K 31/728 | |
| WO | 2017100470 | A1 | 6/2017 | |
| WO | 2021003223 | A1 | 1/2021 | |
| WO | 2023201335 | A2 | 10/2023 | |
| WO | 2023201336 | A2 | 10/2023 | |

OTHER PUBLICATIONS

International Search Report and Written Opinion for International PCT Application No. PCT/US2019/021460, mailed May 24, 2019 (10 pages).

Merrifield, "Solid Phase Peptide Synthesis. I. The Synthesis of a Tetrapeptide," Journal of the American Chemical Society, 85(14), pp. 2149-2154 (1963).

Minto et al., "Pharmacokinetics and Pharmacodynamics of Nandrolone Esters in Oil Vehicle: Effects of Ester, Injection Site and Injection Volume," J. Pharmacol. Exp. Ther., 281, pp. 93-102 (1997).

Morgen et al., "Nanoparticles for Improved Local Retention after Intra-Articular Injection into the Knee Joint," Pharmaceutical Research, 30, pp. 257-268 (2013).

Ostro and Cullis, "Use of liposomes as injectable-drug delivery systems," Am. J. Hosp. Pharm., 46, pp. 1576-1587 (1989).

Presle et al., "Cartilage protection by nitric oxide synthase inhibitors after intraarticular injection of interleukin-1 beta in rats," Arthritis Rheum., 42(10), pp. 2094-2102 (1999).

Rao, "Recent developments of collagen-based materials for medical applications and drug delivery systems," J. Biomater. Sci. Polym. Ed., 7, pp. 623-645 (1995).

Urech et al., "Anti-inflammatory and cartilage-protecting effects of an intra-articularly injected anti-TNFα single-chain Fv antibody (ESBA105) designed for local therapeutic use," Ann. Rheum. Dis., 69(2), pp. 443-449 (2010).

International Search Report and Written Opinion received for PCT Application No. PCT/US2009/038446, mailed on Dec. 14, 2009, 10 pages.

International Search Report and Written Opinion received for PCT Application No. PCT/US2016/065653, mailed on Feb. 24, 2017, 10 pages.

International Search Report and Written Opinion received for PCT Application No. PCT/US2020/040430, mailed on Oct. 1, 2020, 10 pages.

Altiok Eda I. (Oct. 2015) "Improving Anti-VEGF Drugs in the Vitreous", Dissertation, UC Berkeley, 94 pages.

Altiok et al. (Jul. 2016) "Multivalent Hyaluronic Acid Bioconjugates Improve sFlt-1 Activity in Vitro", Biomaterials, 93:95-105(27 pages).

Aoyagi et al. (1999) "Peptide Drug Carrier: Studies on Incorporation of Vasopressin into Nano-associates Comprising Poly(ethylene glycol)-poly (L-aspartic acid) Block Copolymer", Colloids and Surfaces B: Biointerfaces, 16(1-4):237-242.

Arpicco et al. (2002) "Novel Poly(ethylene glycol) Derivatives for Preparation of Ribosome-Inactivating Protein Conjugates", Bioconjugate Chemistry, 13(4):757-765.

Cairo et al. (Feb. 2, 2002) "Control of Multivalent Interactions by Binding Epitope Density", Journal of the American Chemical Society, 124(8):1615-1619.

Chen et al. (1997) "Mitogenic Activities of Water-Soluble and-Insoluble Insulin Conjugates", Bioconjugate Chemistry, 8(2):106-110.

Gestwicki et al. (2002) "Influencing Receptor-Ligand Binding Mechanisms with Multivalent Ligand Architecture", Journal of the American Chemical Society, 124(50):14922-14933.

Glass et al. (Jun. 1996) "Characterization of a Hyaluronic Acid-Arg-Gly-Asp Peptide Cell Attachment Matrix", Biomaterials, 17(11):1101-1108.

Itoda et al. (Jan. 2003) "Evaluation of the Molecular Recognition of Peptide-Conjugated Polymer", Analytical Sciences, 19(1):185-187.

Line et al. (Sep. 2005) "Targeting Tumor Angiogenesis: Comparison of Peptide and Polymer-Peptide Conjugates", Journal of Nuclear Medicine, 46(9):1552-1560.

Mammen et al. (1998) "Polyvalent Interactions in Biological Systems: Implications for Design and Use of Multivalent Ligands and Inhibitors", Angewandte Chemie International Edition, 37(20):2754-2794.

Mitra et al. (2006) "Polymer-Peptide Conjugates for Angiogenesis Targeted Tumor Radiotherapy", Nuclear Medicine and Biology, 33:43-52.

Payne et al. (Apr. 2012) "Expression of Recombinant Canine sFlt1 as an Experimental Anti-angiogenic Agent", The FASEB Journal, 26(1):2 pages.

Shahangian et al. (Mar. 2015) "A Conformation-Based Phage-Display Panning to Screen Neutralizing Anti-VEGF VHHs with VEGFR2 Mimicry Behavior", International Journal of Biological Macromolecules, 77:222-234.

Smith et al. (2003) "Conjugation of Arginine-Glycine-Aspartic Acid Peptides to Thermoreversible N-Isopropylacrylamide Polymers", Journal of Polymer Science: Part A: Polymer Chemistry, 41(24):3989-4000.

Wall et al. (2008) "Multivalency of Sonic Hedgehog Conjugated to Linear Polymer Chains Modulates Protein Potency", Bioconjugate Chemistry, 19(4):806-812.

Yu et al. (2015) "Injectable Chemically Crosslinked Hydrogel for the Controlled Release of Bevacizumab in Vitreous: A 6-Month In Vivo Study", Translational Vision Science and Technology, Article 5, 4(2):11 pages.

Jha et al., "Perlecan domain I-conjugated, hyaluronic acid-based hydrogel particles for enhanced chondrogenic differentiation via BMP-2 release", Biomaterials, 2009, 30(36), 6964-6975.

Magalhães et al., "Methods of Endotoxin Removal from Biological Preparations: a Review." J. Pharm. Pharmaceut. Sci., 2007, pp. 388-404.

Schneier et al., "Current technologies to endotoxin detection and removal for biopharmaceutical purification," Biotechnology and Bioengineering, Apr. 25, 2020, 117(8), pp. 2588-2609.

Sweander et al., "Filtration Removal of Endotoxin (Pyrogens) in Solution in Different States of Aggregation," Applied and Environmental Microbiology, Oct. 1977, 34(4), pp. 382-385.

* cited by examiner

FIG. 2A

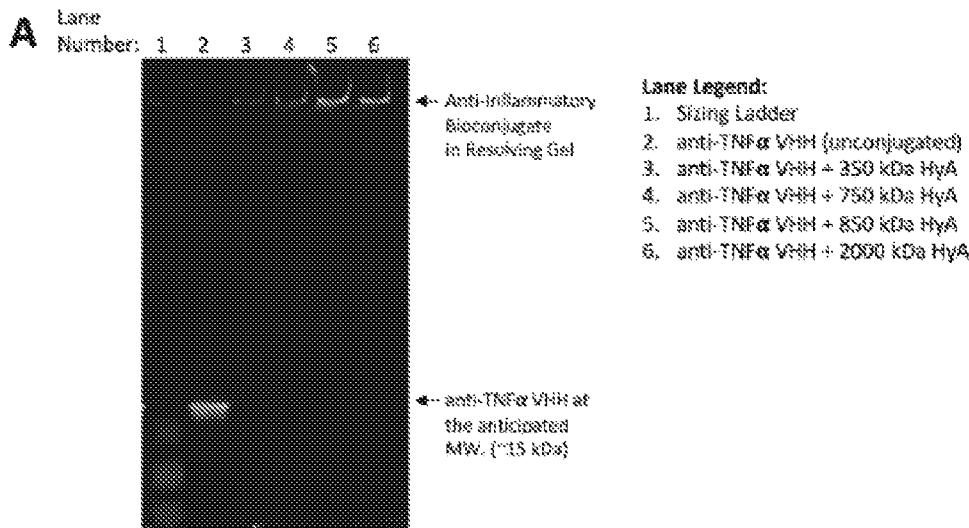

A  Lane
Number:  1  2  3  4  5  6

← Anti-Inflammatory
Bioconjugate
in Resolving Gel

← anti-TNFα VHH at
the anticipated
MW. (~15 kDa)

Lane Legend:
1. Sizing Ladder
2. anti-TNFα VHH (unconjugated)
3. anti-TNFα VHH + 350 kDa HyA
4. anti-TNFα VHH + 750 kDa HyA
5. anti-TNFα VHH + 850 kDa HyA
6. anti-TNFα VHH + 2000 kDa HyA

FIG. 2B

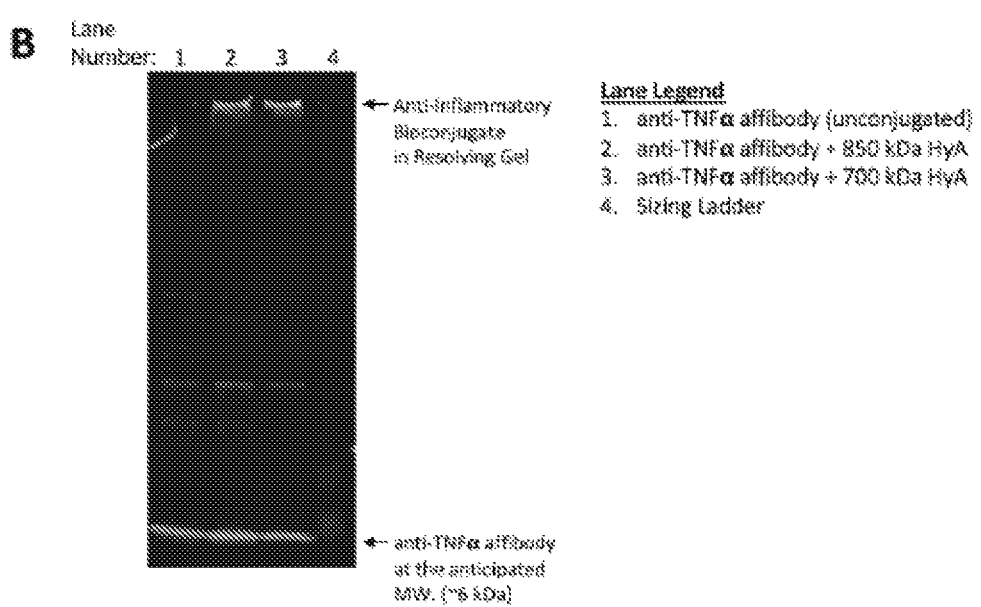

B  Lane
Number:  1  2  3  4

← Anti-Inflammatory
Bioconjugate
in Resolving Gel

← anti-TNFα affibody
at the anticipated
MW. (~8 kDa)

Lane Legend
1. anti-TNFα affibody (unconjugated)
2. anti-TNFα affibody + 850 kDa HyA
3. anti-TNFα affibody + 700 kDa HyA
4. Sizing Ladder

C

Lane
Number:   1    2    3

←— Anti-Inflammatory
Bioconjugate
in Resolving Gel

←— anti-TNFα VHH at
the anticipated
M.W. (~15 kDa)

Lane Legend
1. Sizing Ladder
2. anti-TNFα VHH (unconjugated)
3. anti-TNFα VHH + 200 kDa CM Chitosan

D

Lane
Number:   1    2    3

←— Anti-Inflammatory
Bioconjugate
in Resolving Gel kDa:
130
95
72
55
43
26
17
10

←— MW of anti-IL1β
scFv (~25 kDa)

Lane Legend
1. Sizing Ladder
2. Anti-IL1β scFv + 850 kDa HyA
3. Anti-IL1β scFv + 700 kDa CMC E  Lane
   Number:  1     2

← Anti-Inflammatory
   Bioconjugate
   In Resolving Gel

← anti-TNFα VHH at
   the anticipated
   MW. (~15 kDa)

Lane Legend
1. anti-TNFα VHH (unconjugated)
2. anti-TNFα VHH + 700 kDa CMC

MULTIVALENT PEPTIDE CONJUGATES FOR SUSTAINED INTRA-ARTICULAR TREATMENT OF JOINT INFLAMMATION

CROSS-REFERENCES TO RELATED APPLICATIONS

This application is a U.S. National Phase Application of PCT International Application No. PCT/US2019/021460, filed Mar. 8, 2019, which is an International Application of and claims the benefit of priority to U.S. patent application Ser. No. 62/640,749, filed on Mar. 9, 2018, the entire contents of which are herein incorporated by reference.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 052566-504001WO_SL-ST25.txt. The text file is 14,890 bytes, was created on Mar. 8, 2019, and is being submitted electronically via EFS-Web.

BACKGROUND OF THE INVENTION

There are two routes of administration that may be used to deliver a drug therapy to the tissues of an articular joint: (1) systemic administration (i.e., oral, subcutaneous, and intravenous), or (2) intra-articular injection.

The advantage of systemic administration is that it can be performed easily, often by the patient at home, and thus re-dosing the patient is not a challenge. However, for potent drug products, high systemic levels of the drugs may not be desirable because the high systemic levels that are required to maintain a therapeutic dose in the diseased joint may also cause dangerous side effects elsewhere in the body.

The advantage of intra-articular administration is that potent drugs can be delivered directly into the diseased joint. The dose delivered directly into the joint can be lower than would be required to achieve the same therapeutic effect after systemic administration because the drug has been administered locally to the target tissue. However, intra-articular administration requires a professional to safely provide the injection into the joint tissues. Thus intra-articular injections are substantially more burdensome and costly to administer.

An additional challenge for administration to many joints is that the hydrodynamic pressures generated around the articulating tissues cause proteins and small molecules to be rapidly cleared from the fluids in the joint. In fact, the synovial tissues surrounding the joints include lymphatic ducts that can readily collect fluid and other materials that are exuded from the joint space. As a result, drugs that are administered to the intra-articular space are rapidly cleared from the joint and into the blood stream where they can no longer act effectively on the diseased tissues. Therefore, drugs delivered by intra-articular injection need to be re-dosed frequently to maintain efficacy.

Therefore, there is a strong motivation to improve the intra-articular residence time of drugs that are routinely injected into the joint tissues. It may be useful to modify an existing drug in order to increase its residence time within the intra-articular space. By reducing the frequency of intra-articular administration of a drug, it would be possible to reduce the overall risk of complications that are associated with chronic administration the drug. Increasing the duration of bioactivity may also yield enhanced therapeutic outcomes for the drug as well.

A drug that exhibits a longer intra-articular residence time would be preferred by the patient compared to an alternate drug product that must be administered more frequently for an equivalent therapeutic function. While the intra-articular injection is performed under topical anesthesia and is generally not regarded as painful, it is burdensome for the patient to make frequent visits to the clinician's office for the injections. There may also be short-term irritation at the site of injection. Thus, patients would likely exhibit a preference for an equivalent therapy that would require fewer intra-articular injections.

A conjugate comprising a biologically active polypeptide drug and a biocompatible polymer exhibits an intra-articular half-life that is greater than the intra articular half-life of the biologically active polypeptide when it is not conjugated to the biocompatible polymer. Increasing the half-life of the drug would have the effect of increasing the amount of time that the drug is above the concentration threshold required to generate an effective therapeutic response.

The increased half-life of the conjugate in the joint confers certain advantages, including reduced burden on the patient; reduced number and/or frequency of administrations; increased safety; decreased incidence of infection; increased patient compliance; and increased efficacy. In addition, these conjugates may also enable use of polypeptides for treatment of joint diseases and disorders that would not be retained in the joint for sufficient time in an unconjugated form.

BRIEF SUMMARY OF THE INVENTION

Provided herein is a method of treating disease or disorder that is localized within an articular joint. This method involves the intra-articular administration of a bioconjugate comprised of a biopolymer and multiple copies of a bioactive peptide, e.g., an antibody, such that the disease or disorder is treated.

In some embodiments, the present invention provides a method of treating a disease or disorder in an articular joint, the method comprising injecting into the articular joint an effective amount of a conjugate comprising: a biocompatible polymer having a molecular weight of from about 0.1 MDa to about 3 MDa; and a plurality of peptides, wherein the peptide has a molecular weight of from about 5 kDa to about 150 kDa; wherein each peptide is covalently linked to the polymer, and the molar ratio of the peptide to the polymer in the conjugate is at least about 5:1.

In some embodiments, the present invention provides a conjugate of a biocompatible polymer having a molecular weight of from about 0.1 MDa to about 3 MDa; and a plurality of peptides, wherein the peptide has a molecular weight of from about 5 kDa to about 150 kDa; wherein each peptide is covalently linked to the polymer, and the molar ratio of the peptide to the polymer in the conjugate is at least about 5:1.

In one embodiment, the disclosure provides a conjugate comprising a biocompatible polymer having a molecular weight of from about 0.1 MDa to about 2 MDa; and a plurality of peptides, wherein the peptide has a molecular weight of from about 5 kDa to about 100 kDa; wherein each peptide is covalently linked to the polymer, the molecular weight of the polymer is from about 5 kDa to about 50 kDa per peptide, and the molar ratio of the peptide to the polymer in the conjugate is at least about 5:1.

Further provided herein is a pharmaceutical composition comprising the conjugate of the disclosure and a pharmaceutically acceptable excipient, diluent, and/or carrier.

The present disclosure also includes a method of treating a disease or disorder in an articular joint, the method comprising injecting into the articular joint a therapeutically effective amount of a conjugate described herein, or a pharmaceutical composition comprising the conjugate.

In some embodiments, the present invention provides a method of treating a disease or disorder in an articular joint, the method comprising injecting into the articular joint an effective amount of a conjugate comprising: a biocompatible polymer having a molecular weight of from about 0.1 MDa to about 3 MDa; and a plurality of peptides, wherein the peptide has a molecular weight of from about 5 kDa to about 150 kDa; wherein each peptide is covalently linked to the polymer, and the molar ratio of the peptide to the polymer in the conjugate is at least about 5:1. In some embodiments, the biocompatible polymer has a molecular weight of from about 0.1 MDa to about 2 MDa; and a plurality of peptides, wherein the peptide has a molecular weight of from about 5 kDa to about 100 kDa; wherein each peptide is covalently linked to the polymer, the molecular weight of the polymer is from about 5 kDa to about 50 kDa per peptide, and the molar ratio of the peptide to the polymer in the conjugate is at least about 5:1.

BRIEF DESCRIPTION OF THE DRAWINGS

FIG. 2A shows an SDS-PAGE gel that was used to verify covalent binding of an anti-inflammatory anti-TNFα VHH antibody (SEQ ID NO:7) to HyA of various MWs. The gels were run under reducing conditions that will reverse non-covalent interactions, and thus anti-inflammatory bioconjugates will remain at the top of the resolving gel. FIG. 2B shows an SDS-PAGE gel that was used to verify covalent binding of an anti-inflammatory anti-TNFα affibody (SEQ ID NO:6) to HyA and CMC.

DETAILED DESCRIPTION OF THE INVENTION

I. General

Figure 1:
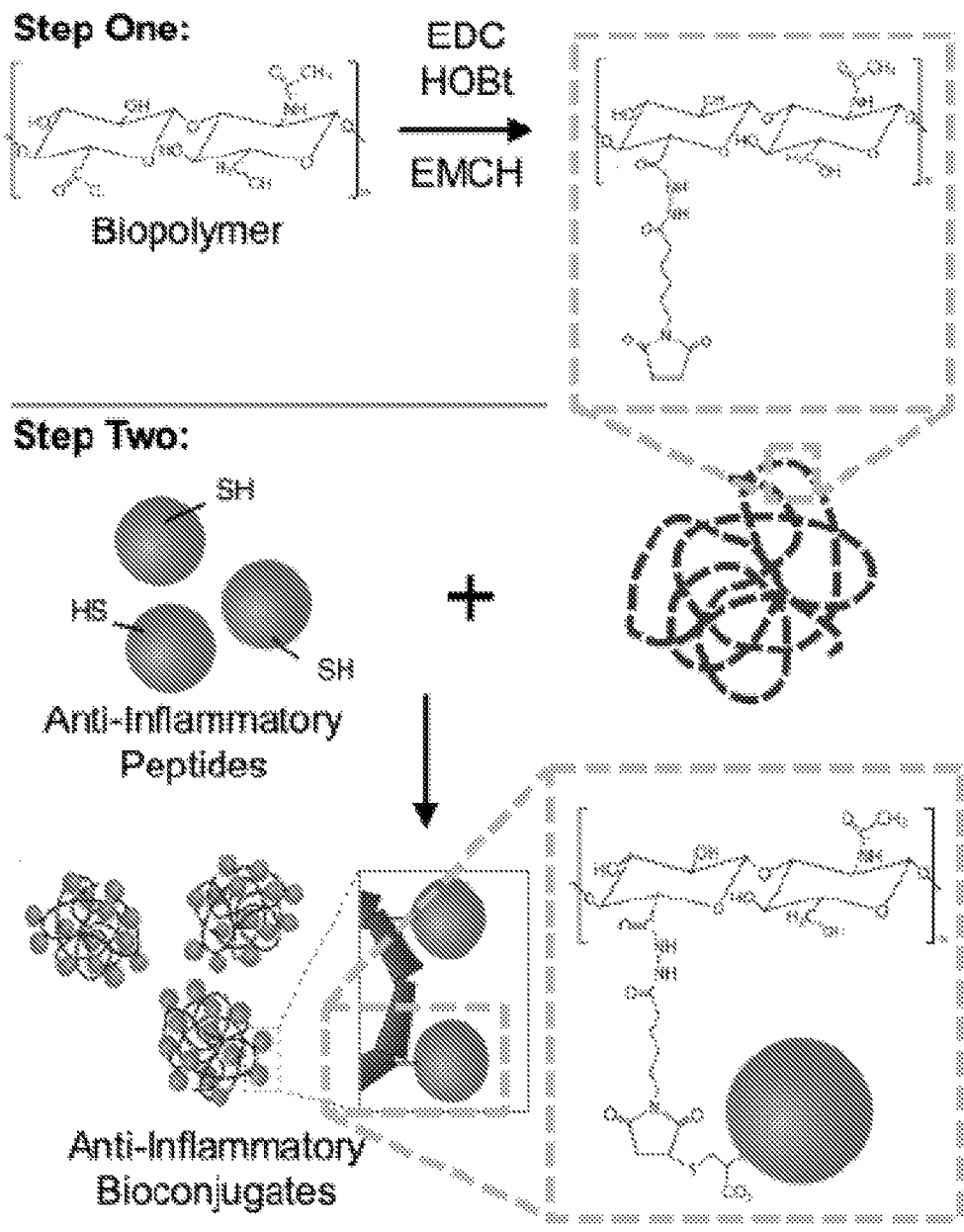
FIG. 1 shows a generalized schematic for the conjugation reactions to generate an anti-inflammatory bioconjugate for use in a method of the present disclosure. Step One consists of the covalent addition of a reactive crosslinker to a specific functional group on a suitable biopolymer. The chemical structure for the biopolymer in this example is HyA, and the crosslinker EMCH is added through carbodiimide chemistry to the carboxylic acid functional group. In the Step Two, the reactive biopolymer is allowed to react with an anti-inflammatory peptide that includes a residue that is targeted for covalent binding to the chemical crosslinker. In this example, the peptides contain a residue that presents a thiol as a target for conjugation.

The present invention provides conjugates of high molecular weight polymers and a plurality of peptides that possess a potency greater than the unconjugated peptide, and an increased half-life allowing the conjugates to treat intra-articular diseases and disorders, among others.

II. Definitions

Unless specifically indicated otherwise, all technical and scientific terms used herein have the same meaning as commonly understood by those of ordinary skill in the art to which this invention belongs. In addition, any method or material similar or equivalent to a method or material described herein can be used in the practice of the present invention. For purposes of the present invention, the following terms are defined.

"HyA" as used herein refers to hyaluronic acid.

"CMC" refers to carboxymethyl cellulose.

"scFV" refers to small chain variable fragment antibody.

"VHH" as used herein refers to a single-domain heavy chain antibody.

"DARPin" refers to a designed ankyrin repeat protein, which is a genetically engineered antibody mimetic protein that can exhibit highly specific and high-affinity target protein binding.

"Articular joint" as used herein refers to the fibrous or cartilaginous joints, which is a fibrous or cartilaginous area wherein two or more bones connect to each other.

"Therapeutically effective amount" as used herein refers to a dose that produces therapeutic effects for which it is administered. The exact dose will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, Dosage Calculations (1999); and Remington: The Science and Practice of Pharmacy, 20th Edition, 2003, Gennaro, Ed., Lippincott, Williams & Wilkins). In sensitized cells, the therapeutically effective dose can often be lower than the conventional therapeutically effective dose for non-sensitized cells.

"Biocompatible polymer" as used herein refers to a polymer compatible with the joints at the injection site. Representative biocompatible polymers include, but are not limited to polysaccharides, glycosaminoglycans, and hyaluronic acid.

"Polymer molecular weight" as used herein refers to the molecular weight of the polymer.

"Peptide," "polypeptide," and "protein" are used interchangeably herein, and refer to naturally occurring and synthetic amino acids of any length, as well as amino acid analogs and amino acid mimetics that function in a manner similar to the naturally occurring amino acids. The term "polypeptide" includes fusion proteins, including, but not limited to, fusion proteins with a heterologous amino acid sequence, fusions with heterologous and homologous leader sequences, with or without N-terminal methionine residues;

immunologically tagged proteins; and the like. The term "polypeptide" includes post-translationally modified polypeptides.

"Modulate" as used herein refers to the ability of a compound to increase or decrease the function, or activity, of the associated activity (e.g., immune cell function).

"Immune cell function" includes, for example, modulation of an immune response. The modulation can be immunosuppressive or immunostimulatory. Examples of immune responses can include, but are not limited to a humoral immune response, a cell-mediate immune response, or an inflammatory response.

"Inhibition", "inhibits" and "inhibitor" as used herein refer to a compound that prohibits or a method of prohibiting, a specific action or function.

"Antibody" as used herein refers to a polypeptide encoded by an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD, and IgE, respectively. Antibodies are representative of a wide variety of receptors including hormone receptors, drug targets such as peripheral benzodiazepine receptor, and carrier proteins. Representative antibodies include, but are not limited to monoclonal IgG antibodies, IgG antibody fragments, single chain scFv antibodies, single-domain heavy-chain VHH antibodies, or engineered antibody-like scaffolds such as adnectins, affibodies, anticalins, DARPins, and engineered Kunitz-type inhibitors. Other examples also include receptor decoys of immunomodulatory cytokines such as Tumor Necrosis Factor-α and IL-1β, IL-6, or interferon-γ.

"Sulfide bond" as used herein refers to any moiety having a sulfur covalent bond.

"Linker" as used herein refers to a chemical moiety that directly or indirectly covalently links the polypeptide to the polymer. Linkers useful in the present invention can be about 100 Da to 500 Da. The types of linkers of the present invention include, but are not limited to, imides, amides, amines, esters, carbamates, ureas, thioethers, thiocarbamates, thiocarbonate and thioureas. One of skill in the art will appreciate that other types of linkers are useful in the present invention.

"Diffusion half-life" as used herein refers to the time it takes for the initial concentration of the conjugate within a given volume or space to decrease by half, where the decrease in concentration is a function of the concentration gradient.

"Intra-articular half-life" as used herein refers to the time it takes for the initial concentration of the conjugate within a particular joint to decrease by half, where the transport out of the joint is via convection. Convective transport is the combination of transport via diffusion and advection, where advective transport is the transport of a substance by bulk motion.

"Pharmaceutical composition" as used herein refers to a product comprising the specified ingredients in the specified amounts, as well as any product, which results, directly or indirectly, from combination of the specified ingredients in the specified amounts. The pharmaceutical composition is generally safe for biological use.

"Pharmaceutically acceptable carrier" and "pharmaceutically acceptable excipient" as used herein refers to a substance that aids the administration of an active agent to an absorption by a subject. Pharmaceutical carrier and/or excipient useful in the present invention include, but are not limited to, binders, fillers, disintegrants, lubricants, coatings, sweeteners, flavors and colors. One of skill in the art will recognize that other pharmaceutical carriers and/or excipients are useful in the present invention.

III. Peptide-Polymer Conjugates

The present invention provides conjugates of high molecular weight polymers and a plurality of peptides that possess a potency greater than a similar concentration of the unconjugated peptide. In some embodiments, the present invention provides a conjugate of a biocompatible polymer having a molecular weight of from about 0.1 MDa to about 3 MDa; and a plurality of peptides, wherein the peptide has a molecular weight of from about 5 kDa to about 150 kDa; wherein each peptide is covalently linked to the polymer, and the molar ratio of the peptide to the polymer in the conjugate is at least about 5:1.

In some embodiments, the biocompatible polymer has a molecular weight of from about 0.1 MDa to about 2 MDa; and a plurality of peptides, wherein the peptide has a molecular weight of from about 5 kDa to about 100 kDa; wherein each peptide is covalently linked to the polymer, the molecular weight of the polymer is from about 5 kDa to about 50 kDa per peptide, and the molar ratio of the peptide to the polymer in the conjugate is at least about 5:1.

Biocompatible Polymers

Polymers useful in the conjugates of the present invention include any suitable biocompatible polymer. Biocompatible polymers are hydrophilic polymers that generally do not trigger an immune response. Suitable biocompatible polymers include, but are not limited to, polysaccharides, glycosaminoglycan, hyaluronic acid and derivatives thereof, cellulose, carboxymethylcellulose and derivatives thereof, heparin and derivatives thereof, dermatin, starch and modified starches, chondroitin, chitosan, carboxymethyl chitosan and others. The biocompatible polymer can also include polyvinylchloride, polytetrafluoroethylene, polyethersulfone, polyethylene, polyetheretherketone, polysulfone, polypropylene, poly(ethylene glycol), poly(propylene glycol), polyurethanes, ethylene vinyl acetate copolymers, collagen, poly isobutylene, ethylene vinyl alcohol copolymers, polyethylene polycarbonate, polycaprolactone, polylactide, polyglycolide, carbomers, polyesters, polyethers, polyanhydrides, polyacrylates, polyvinyl acetates, polyvinyl pyrrolidones, polysaccharides (such as hyaluronic acid, hydroxyalkylcelluloses, carboxyalkylcelluloses, or derivatives thereof), polyether, derivatives thereof and combinations thereof. The biocompatible polymers can be further modified by methods such as sulfation, sulfonation, deuteration, etc.

Polysaccharides useful as the biocompatible polymer include, but are not limited to, cellulose, carboxymethylcellulose, methyl cellulose, hydroxypropyl cellulose, chitin, glycosaminoglycans, chondroitin sulfate, hyaluronan (hyaluronic acid), heparin, heparan sulfate, among others. In some embodiments, the biocompatible polymer can be a polysaccharide. In some embodiments, the biocompatible polymer can be a glycosaminoglycan. In some embodiments, the biocompatible polymer can be hyaluronic acid.

The biocompatible polymer of the present invention can be of any suitable molecular weight. For example, suitable biocompatible polymers can have a molecular weight of from about 0.1 MDa to about 3 MDa, or about 100 kDa to about 3,000 kDa. A polymer molecular weight can typically be expressed as the number average molecular weight ($M_n$) or the weight average molecular weight ($M_w$). The number average molecular weight is the mathematical mean of the molecular masses of the individual macromolecules. The weight average molecular weight is influenced by larger molecules and so is a larger number than the number average molecular weight. The ratio of $M_w/M_n$ is the polydispersity of the polymer and represents the breadth of molecular weights in the polymer sample. Reference to molecular weights in the present invention are to the weight average molecular weight ($M_w$) unless stated otherwise.

Molecular weights useful for biocompatible polymer include, but are not limited to, from about 0.1 MDa to about 3 MDa, from about 0.1 MDa to about 2 MDa, from about 0.2 MDa to about 1.5 MDa, from about 0.8 MDa to about 3 MDa, from about 1 MDa to about 3 MDa, from about 1.5 MDa to about 3 MDa, or from about 1 MDa to about 2 MDa. In some embodiments, the biocompatible polymer has a molecular weight of from about 0.1 MDa to about 3 MDa. In some embodiments, the biocompatible polymer has a molecular weight of from about 0.1 MDa to about 2 MDa. In some embodiments, the biocompatible polymer has a molecular weight of from about 0.2 MDa to about 1.5 MDa. In some embodiments, the biocompatible polymer has a molecular weight of from about 0.8 MDa to about 3 MDa. The biocompatible polymer can have a molecular weight of about 0.1 MDa, or 0.2, 0.25, 0.3, 0.35, 0.4, 0.45, 0.5, 0.55, 0.6, 0.65, 0.7, 0.75, 0.8, 0.85, 0.9, 0.95, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, or about 3 MDa. In some embodiments, the biocompatible polymer has a molecular weight of at least about 0.85 MDa. In some embodiments, the biocompatible polymer has a molecular weight of about 0.9 MDa. In some embodiments, the biocompatible polymer has a molecular weight of at least about 1 MDa. In some embodiments, the biocompatible polymer has a molecular weight of about 2 MDa.

The biocompatible polymer can have a molecular weight of from about 5 kDa to about 600 kDa per peptide, or from about 5 kDa to 500 kDa, from about 5 kDa to about 400 kDa, from about 5 kDa to about 300 kDa, from about 5 kDa to about 200 kDa, to about 5 kDa to about 100 kDa, from about 5 kDa to about 50 kDa, from about 5 kDa to about 40 kDa, from about 5 kDa to about 30 kDa, from about 5 kDa to about 20 kDa, or from about 5 kDa to about 10 kDa per peptide. The biocompatible polymer can have a molecular weight per peptide of about 5 kDa, or 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, or about 100 kDa.

Peptides

Peptides suitable in the present invention are those having a molecular weight of at least about 2 kDa, and exhibit tertiary structure. Representative peptides include, but are not limited to, polypeptides, one or more aptamers, avimer scaffolds based on human A domain scaffolds, diabodies, camelids, shark IgNAR antibodies, fibronectin type III scaffolds with modified specificities, antibodies, antibody fragments, proteins, peptides, polypeptides.

In one particularly useful embodiment, the peptide is a therapeutic protein. Numerous therapeutic proteins are disclosed throughout the application such as, and without limitation, erythropoietin, granulocyte colony stimulating factor (G-CSF), GM-CSF, interferon alpha, interferon beta, human growth hormone, and imiglucerase.

In one embodiment, the peptide can be selected from specifically identified protein or peptide agents, including, but not limited to: Aβ, agalsidase, alefacept, alkaline phosphatase, aspariginase, amdoxovir (DAPD), antide, becaplermin, botulinum toxin including types A and B and lower molecular weight compounds with botulinum toxin activity, calcitonins, cyanovirin, denileukin diftitox, erythropoietin (EPO), EPO agonists, dornase alpha, erythropoiesis stimulating protein (NESP), coagulation factors such as Factor V, Factor VII, Factor VIIa, Factor VIII, Factor IX, Factor X, Factor XII, Factor XIII, von Willebrand factor; ceredase, cerezyme, alpha-glucosidase, N-Acetylgalactosamine-6-sulfate sulfatase, collagen, cyclosporin, alpha defensins, beta defensins, desmopressin, exendin-4, cytokines, cytokine receptors, granulocyte colony stimulating factor (G-CSF), thrombopoietin (TPO), alpha-1 proteinase inhibitor, elcatonin, granulocyte macrophage colony stimulating factor (GM-CSF), fibrinogen, filgrastim, growth hormones human growth hormone (hGH), somatropin, growth hormone releasing hormone (GHRH), GRO-beta, GRO-beta antibody, bone morphogenic proteins such as bone morphogenic protein-2, bone morphogenic protein-6, parathyroid hormone, parathyroid hormone related peptide, OP-1; acidic fibroblast growth factor, basic fibroblast growth factor, Fibroblast Growth Factor 21, CD-40 ligand, heparin, human serum albumin, low molecular weight heparin (LMWH), interferon alpha, interferon beta, interferon gamma, interferon omega, interferon tau, consensus interferon, human lysyl oxidase-like-2 (LOXL2); interleukins and interleukin receptors such as interleukin-1 receptor, interleukin-2, interleukin-2 fusion proteins, interleukin-1 receptor antagonist, interleukin-3, interleukin-4, interleukin-4 receptor, interleukin-6, interleukin-8, interleukin-12, interleukin-17, interleukin-21, interleukin-23, p40, interleukin-13 receptor, interleukin-17 receptor; lactoferrin and lactoferrin fragments, luteinizing hormone releasing hormone (LHRH), insulin, pro-insulin, insulin analogues, leptin, ghrelin, amylin, C-peptide, somatostatin, somatostatin analogs including octreotide, vasopressin, follicle stimulating hormone (FSH), imiglucerase, influenza vaccine, insulin-like growth factor (IGF), insulintropin, macrophage colony stimulating factor (M-CSF), plasminogen activators such as alteplase, urokinase, reteplase, streptokinase, pamiteplase, lanoteplase, and teneteplase; nerve growth factor (NGF), osteoprotegerin, platelet-derived growth factor, tissue growth factors, transforming growth factor-1, vascular endothelial growth factor, leukemia inhibiting factor, keratinocyte growth factor (KGF), glial growth factor (GGF), T Cell receptors, CD molecules/antigens, tumor necrosis factor (TNF) (e.g., TNF-α and TNF-β), TNF receptors (e.g., TNF-α receptor and TNF-β receptor), CTLA4, CTLA4 receptor, monocyte chemoattractant protein-1, endothelial growth factors, parathyroid hormone (PTH), glucagon-like peptide, somatotropin, thymosin alpha 1, rasburicase, thymosin alpha 1 Hb/IIIa inhibitor, thymosin beta 10, thymosin beta 9, thymosin beta 4, alpha-1 antitrypsin, phosphodiesterase (PDE) compounds, VLA-4 (very late antigen-4), VLA-4 inhibitors, bisphosphonates, respiratory syncytial virus antibody, cystic fibrosis transmembrane regulator (CFTR) gene, deoxyribonuclease (Dnase), bactericidal/permeability increasing protein (BPI), and anti-CMV antibody. Exemplary monoclonal antibodies include etanercept (a dimeric fusion protein consisting of the extracellular ligand-binding portion of the human 75 kD TNF receptor linked to the Fc portion of IgG1), abciximab, adalimumab, afelimomab, alemtuzumab, antibody to B-lymphocyte, atlizumab, basiliximab, bevacizumab, biciromab, bertilimumab, CDP-484, CDP-571, CDP-791, CDP-860, CDP-870, cetuximab, clenoliximab, daclizumab, eculizumab, edrecolomab, efalizumab, epratuzumab, fontolizumab, gavilimomab, gemtuzumab ozogamicin, ibritumomab tiuxetan, infliximab, inolimomab, keliximab, labetuzumab, lerdelimumab, olizumab, radiolabeled lym-1, metelimumab, mepolizumab, mitumomab, muromonad-CD3, nebacumab, natalizumab, odulimomab, omalizumab, oregovomab, palivizumab, pemtumomab, pexelizumab, rhuMAb-VEGF, rituximab, satumomab pendetide, sevirumab, siplizumab, tositumomab, I.sup.131tositumomab, trastuzumab, tuvirumab, visilizumab, and fragments and mimetics thereof.

In one embodiment, the peptide is a fusion protein. For example, and without limitation, the peptide can be an immunoglobulin or portion of an immunoglobulin fused to one or more certain useful peptide sequences. For example, the peptide may contain an antibody Fc fragment. In one embodiment, the peptide is a CTLA4 fusion protein. For example, the peptide can be an Fc-CTLA4 fusion protein. In another embodiment, the peptide is a Factor VIII fusion protein. For example, the peptide can be an Fc-Factor VIII fusion protein.

In one particularly useful embodiment, the peptide is a human protein or human polypeptide, for example, a heterologously produced human protein or human polypeptide. Numerous proteins and polypeptides are disclosed herein for which there is a corresponding human form (i.e., the protein or peptide is normally produced in human cells in the human body). Therefore, in one embodiment, the peptide is the human form of each of the proteins and polypeptides disclosed herein for which there is a human form. Examples of such human proteins include, without limitation, human antibodies, human enzymes, human hormones and human cytokines such as granulocyte colony stimulation factor, granulocyte macrophage colony stimulation factor, interferons (e.g., alpha interferons and beta interferons), human growth hormone and erythropoietin.

Other examples of therapeutic proteins include, without limitation, factor VIII, b-domain deleted factor VIII, factor VIIa, factor IX, anticoagulants; hirudin, alteplase, tpa, reteplase, tpa, tpa-3 of 5 domains deleted, insulin, insulin lispro, insulin aspart, insulin glargine, long-acting insulin analogs, hgh, glucagons, tsh, follitropin-beta, fsh, gm-csf, pdgh, ifn alpha2, ifn alpha2a, ifn alpha2b, inf-aphal, consensus ifn, ifn-beta, ifn-beta 1b, ifn-beta 1a, ifn-gamma (e.g., 1 and 2), ifn-lambda, ifn-delta, it-2, it-11, hbsag, ospa, murine mab directed against t-lymphocyte antigen, murine mab directed against tag-72, tumor-associated glycoprotein, fab fragments derived from chimeric mab directed against platelet surface receptor gpII(b)/III(a), murine mab fragment directed against tumor-associated antigen cal 25, murine mab fragment directed against human carcinoembryonic antigen, cea, murine mab fragment directed against human cardiac myosin, murine mab fragment directed against tumor surface antigen psma, murine mab fragments (fab/fab2 mix) directed against hmw-maa, murine mab fragment (fab) directed against carcinoma-associated antigen, mab fragments (fab) directed against nca 90, a surface granulocyte nonspecific cross reacting antigen, chimeric mab directed against cd20 antigen found on surface of b lymphocytes, humanized mab directed against the alpha chain of the i12 receptor, chimeric mab directed against the alpha chain of the i12 receptor, chimeric mab directed against tnf-alpha, humanized mab directed against an epitope on the surface of respiratory synctial virus, humanized mab directed against her 2, human epidermal growth factor receptor 2, human mab directed against cytokeratin tumor-associated antigen anti-ctla4, chimeric mab directed against cd 20 surface antigen of b lymphocytes dornase-alpha dnase, beta glucocerebrosidase, tnf-alpha, il-2-diptheria toxin fusion protein, tnfr-lgg fragment fusion protein laronidase, dnaases, alefacept, darbepoetin alpha (colony stimulating factor), tositumomab, murine mab, alemtuzumab, rasburicase, agalsidase beta, teriparatide, parathyroid hormone derivatives, adalimumab (lggl), anakinra, biological modifier, nesiritide, human b-type natriuretic peptide (hbnp), colony stimulating factors, pegvisomant, human growth hormone receptor antagonist, recombinant activated protein c, omalizumab, immunoglobulin e (lge) blocker, lbritumomab tiuxetan, ACTH, glucagon, somatostatin, somatotropin, thymosin, parathyroid hormone, pigmentary hormones, somatomedin, erythropoietin, luteinizing hormone, chorionic gonadotropin, hypothalmic releasing factors, etanercept, antidiuretic hormones, prolactin and thyroid stimulating hormone. And any of these can be modified to have a site-specific conjugation point (a N-terminus, or C-terminus, or other location) using natural (for example, a serine to cysteine substitution) (for example, formylaldehyde per method of Redwood Biosciences) or non-natural amino acid.

Examples of therapeutic antibodies (or their respective scFv or Fab fragments) useful in the present invention include, but are not limited to, Anti-TNF inhibitors such as the TNF receptor decoy etanercept and the monoclonal antibodies adalimumab, infliximab, golimumab, and certolizumab, the IL-6 monoclonal antibody inhibitor siltuximab, the IL-17 monoclonal antibody inhibitors secukinumab and ixekizumab, the IL-12/23 monoclonal antibody inhibitor ustekinumab, integrin receptor antagonists such as the monoclonal antibody inhibitors natalizumab and etrolizumab, the CLTA receptor antagonist abatacept, the IL-13 monoclonal antibody inhibitor tralokinumab, chemokine inhibitors such as the monoclonal antibodies eldelumab and bertilumab, and IL-1 inhibitors such as the receptor decoy rilonacept and the such as the monoclonal antibody canakinumab.

Other examples of therapeutic antibodies (or their respective scFv or Fab fragments) useful in the present invention include, but are not limited, to HERCEPTIN™ (Trastuzumab) (Genentech, CA) which is a humanized anti-HER2 monoclonal antibody for the treatment of patients with metastatic breast cancer; REOPRO™ (abciximab) (Centocor) which is an anti-glycoprotein IIb/IIIc receptor on the platelets for the prevention of clot formation; ZENA-PAX™ (daclizumab) (Roche Pharmaceuticals, Switzerland) which is an immunosuppressive, humanized anti-CD25 monoclonal antibody for the prevention of acute renal allograft rejection; PANOREX™ which is a murine anti-17-IA cell surface antigen IgG2a antibody (Glaxo Wellcome/Centocor); BEC2 which is a murine anti-idiotype (GD3 epitope) IgG antibody (ImClone System); IMC-C225 which is a chimeric anti-EGFR IgG antibody (ImClone System); VITAXIN™ which is a humanized anti-αVβ3 integrin antibody (Applied Molecular Evolution/MedImmune); Campath; Campath 1H/LDP-03 which is a humanized anti CD52 IgG1 antibody (Leukosite); Smart M195 which is a humanized anti-CD33 IgG antibody (Protein Design Lab/Kanebo); RITUXAN™ which is a chimeric anti-CD2O IgG1 antibody (IDEC Pharm/Genentech, Roche/Zettyaku); LYMPHOCIDE™ which is a humanized anti-CD22 IgG antibody (Immunomedics); ICM3 is a humanized anti-ICAM3 antibody (ICOS Pharm); IDEC-114 is a primate anti-CD80 antibody (IDEC Pharm/Mitsubishi); ZEVA-LIN™ is a radiolabelled murine anti-CD20 antibody (IDEC/Schering AG); IDEC-131 is a humanized anti-CD40L antibody (IDEC/Eisai); IDEC-151 is a primatized anti-CD4 antibody (IDEC); IDEC-152 is a primatized anti-CD23 antibody (IDEC/Seikagaku); SMART anti-CD3 is a humanized anti-CD3 IgG (Protein Design Lab); 5G1.1 is a humanized anti-complement factor 5 (CS) antibody (Alexion Pharm); D2E7 is a humanized anti-TNF-α antibody (CATI-BASF); CDP870 is a humanized anti-TNF-α Fab fragment (Celltech); IDEC-151 is a primatized anti-CD4 IgG1 antibody (IDEC Pharm/SmithKline Beecham); MDX-CD4 is a human anti-CD4 IgG antibody (Medarex/Eisai/Genmab); CDP571 is a humanized anti-TNF-α IgG4 antibody (Celltech); LDP-02 is a humanized anti-α4β7 antibody (LeukoSite/Genentech); OrthoClone OKT4A is a humanized anti-CD4 IgG antibody (Ortho Biotech); ANTOVA™ is a humanized anti-CD40L IgG antibody (Biogen); ANTE-GREN™ is a humanized anti-VLA-4 IgG antibody (Elan); CAT-152, a human anti-TGF-β.sub.2 antibody (Cambridge Ab Tech); Cetuximab (BMS) is a monoclonal anti-EGF receptor (EGFr) antibody; Bevacizuma (Genentech) is an anti-VEGF human monoclonal antibody; Infliximab (Centocore, JJ) is a chimeric (mouse and human) monoclonal antibody used to treat autoimmune disorders; Gemtuzumab ozogamicin (Wyeth) is a monoclonal antibody used for chemotherapy; and Ranibizumab (Genentech) is a chimeric (mouse and human) monoclonal antibody used to treat macular degeneration.

Proteins and peptides disclosed herein can be produced by any useful method including production by in vitro synthesis and by production in biological systems. Typical examples of in vitro synthesis methods which are well known in the art include solid-phase synthesis ("SPPS") and solid-phase fragment condensation ("SPFC"). Biological systems used for the production of proteins are also well known in the art. Bacteria (e.g., *E. coli* and *Bacillus* sp.), yeast (e.g., *Saccharomyces cerevisiae* and *Pichia pastoris*) tobacco leaves (via tobacco mosaic virus) are widely used for the production of heterologous proteins. In addition, heterologous gene expression for the production of peptides for use as disclosed herein can be accomplished using animal cell lines such as mammalian cell lines (e.g., CHO cells). In one particularly useful embodiment, the peptides are produced in transgenic or cloned animals such as cows, sheep, goats and birds (e.g., chicken, quail, ducks and turkey), each as is understood in the art. See, for example, U.S. Pat. No. 6,781,030, issued Aug. 24, 2004, the disclosure of which is incorporated in its entirety herein by reference.

Protein or polypeptides useful in the present invention may also comprise non-naturally occurring amino acids in addition to the common naturally occurring amino acids found in proteins and polypeptides. In addition to being present for the purpose of altering the properties of a polypeptide or protein, non-naturally occurring amino acids can be introduced to provide a functional group that can be used to link the protein or polypeptide directly to the random copolymer. Furthermore, naturally occurring amino acids, e.g., cysteine, tyrosine, tryptophan can be used in this way.

Non-naturally occurring amino acids can be introduced into proteins and peptides by a variety of means. Some of the techniques for the introduction of non-natural amino acids are discussed in U.S. Pat. No. 5,162,218, the disclosure of which is incorporated in its entirety herein by reference. First, non-naturally occurring amino acids can be introduced by chemical modification of a polypeptide or protein on the amino acid side chain or at either the amino terminus or the carboxyl terminus. Non-limiting examples of chemical modification of a protein or peptide might be methylation by agents such as diazomethane, or the introduction of acetylation at an amino group present in lysine's side chain or at the amino terminus of a peptide or protein. Another example of the protein/polypeptide amino group modification to prepare a non-natural amino acid is the use of methyl 3-mercaptopropionimidate ester or 2-iminothiolane to introduce a thiol (sulfhydryl, —SH) bearing functionality linked to positions in a protein or polypeptide bearing a primary amine. Once introduced, such groups can be employed to form a covalent linkage to the protein or polypeptide.

Second, non-naturally occurring amino acids can be introduced into proteins and polypeptides during chemical synthesis. Synthetic methods are typically utilized for preparing polypeptides having fewer than about 200 amino acids, usually having fewer than about 150 amino acids, and more usually having 100 or fewer amino acids. Shorter proteins or polypeptides having less than about 75 or less than about 50 amino acids can be prepared by chemical synthesis.

The synthetic preparation methods that are particularly convenient for allowing the insertion of non-natural amino acids at a desired location are known in the art. Suitable synthetic polypeptide preparation methods can be based on Merrifield solid-phase synthesis methods where amino acids are sequentially added to a growing chain (Merrifield (1963) J. Am. Chem. Soc. 85:2149-2156). Automated systems for synthesizing polypeptides by such techniques are now commercially available from suppliers such as Applied Biosystems, Inc., Foster City, Calif. 94404; New Brunswick Scientific, Edison, N.J. 08818; and Pharmacia, Inc., Biotechnology Group, Piscataway, N.J. 08854.

Examples of non-naturally occurring amino acids that can be introduced during chemical synthesis of polypeptides include, but are not limited to: D-amino acids and mixtures of D and L-forms of the 20 naturally occurring amino acids, N-formyl glycine, ornithine, norleucine, hydroxyproline, beta-alanine, hydroxyvaline, norvaline, phenylglycine, cyclohexylalanine, t-butylglycine (t-leucine, 2-amino-3,3-dimethylbutanoic acid), hydroxy-t-butylglycine, amino butyric acid, cycloleucine, 4-hydroxyproline, pyroglutamic acid (5-oxoproline), azetidine carboxylic acid, pipecolinic acid, indoline-2-carboxylic acid, tetrahydro-3-isoquinoline carboxylic acid, 2,4-diaminobutyricacid, 2,6-diaminopimelic acid, 2,4-diaminobutyricacid, 2,6-diaminopimelicacid, 2,3-diaminopropionicacid, 5-hydroxylysine, neuraminic acid, and 3,5-diiodotyrosine.

Third, non-naturally occurring amino acids can be introduced through biological synthesis in vivo or in vitro by insertion of a non-sense codon (e.g., an amber or ocher codon) in a DNA sequence (e.g., the gene) encoding the polypeptide at the codon corresponding to the position where the non-natural amino acid is to be inserted. Such techniques are discussed for example in U.S. Pat. Nos. 5,162,218 and 6,964,859, the disclosures of which are incorporated in their entirety herein by reference. A variety of methods can be used to insert the mutant codon including oligonucleotide-directed mutagenesis. The altered sequence is subsequently transcribed and translated, in vivo or in vitro in a system which provides a suppressor tRNA, directed against the nonsense codon that has been chemically or enzymatically acylated with the desired non-naturally occurring amino acid. The synthetic amino acid will be inserted at the location corresponding to the nonsense codon. For the preparation of larger and/or glycosylated polypeptides, recombinant preparation techniques of this type are usually preferred. Among the amino acids that can be introduced in this fashion are: formyl glycine, fluoroalanine, 2-Amino-3-mercapto-3-methylbutanoic acid, homocysteine, homoarginine and the like. Other similar approaches to obtain non-natural amino acids in a protein include methionine substitution methods.

Where non-naturally occurring amino acids have a functionality that is susceptible to selective modification, they are particularly useful for forming a covalent linkage to the protein or polypeptide. Circumstances where a functionality is susceptible to selective modification include those where the functionality is unique or where other functionalities that might react under the conditions of interest are hindered either stereochemically or otherwise.

Other antibodies, such as single domain antibodies are useful in the present invention. A single domain antibody (sdAb, called Nanobody by Ablynx) is an antibody fragment consisting of a single monomeric variable antibody domain. Like a whole antibody, the sdAb is able to bind selectively to a specific antigen. With a molecular weight of only 12-15 kDa, single domain antibodies are much smaller than common whole antibodies (150-160 kDa). A single domain antibody is a peptide chain of about 110 amino acids in length, comprising one variable domain (VH) of a heavy chain antibody, or of a common IgG.

Unlike whole antibodies, single domain antibody (sdAbs) such as VHH do not show complement system triggered cytotoxicity because they lack an Fc region. Camelid and fish derived sdAbs are able to bind to hidden antigens that are not accessible to whole antibodies, for example to the active sites of enzymes.

A sdAb can be obtained by immunization of dromedaries, camels, llamas, alpacas or sharks with the desired antigen and subsequent isolation of the mRNA coding for heavy chain antibodies. Alternatively they can be made by screening synthetic libraries. Camelids are members of the biological family Camelidae, the only living family in the suborder Tylopoda. Camels, dromedaries, Bactrian Camels, llamas, alpacas, vicunas, and guanacos are in this group.

Peptides useful in the present invention also include, but are not limited to, a macrocyclic peptide, a cyclotide, an LDL receptor A-domain, a soluble receptor, an enzyme, a peptide multimer, a domain multimer, an antibody fragment multimer, and a fusion protein.

In some embodiments, the peptide modulates the activity of immune cell function. In some embodiments, the peptide inhibits tumor necrosis factor-α, interleukin-1β, interleukin-6, or interferon-γ. In some embodiments, the peptide inhibits tumor necrosis factor-α. In some embodiments, the peptide is a monoclonal IgG antibody, an IgG antibody fragment, a single-chain variable region antibody, a single-domain heavy chain antibody, an adnectin, an affibody, an anticalin, a DARPin, a Kunitz-type inhibitor, or a receptor decoy.

In some embodiments, the peptide can be anti-TNFα single-domain heavy-chain (VHH) antibody. In some embodiments, the peptide can be anti-TNFα affibody. In some embodiments, the peptide can be anti-TNFα designed ankyrin repeat protein (DARPin). In some embodiments, the peptide can be anti-IL-1B single-chain (scFv) antibody. In some embodiments, the peptide can be soluble interleukin receptor 2 (sILR2). In some embodiments, the peptide has an amino acid sequence that is SEQ ID NO:1, SEQ ID NO:2, SEQ ID NO:6, SEQ ID NO:7, SEQ ID NO:8, SEQ ID NO:9, SEQ ID NO:10 or SEQ ID NO:11. In some embodiments, the peptide has an amino acid sequence that is SEQ ID NO:1, SEQ ID NO:2, SEQ ID NO:6, SEQ ID NO:7, SEQ ID NO:8, SEQ ID NO:9, or SEQ ID NO:10. In some embodiments, the peptide has an amino acid sequence that is SEQ ID NO:1, SEQ ID NO:2, SEQ ID NO:6, SEQ ID NO:7, SEQ ID NO:9, SEQ ID NO:10 or SEQ ID NO:11. In some embodiments, the peptide has an amino acid sequence that is SEQ ID NO:6, SEQ ID NO:7, SEQ ID NO:9, or SEQ ID NO:11. In some embodiments, the peptide has an amino acid sequence that is SEQ ID NO:6, SEQ ID NO:7, or SEQ ID NO:9. In some embodiments, the peptide has an amino acid sequence that is SEQ ID NO:6. In some embodiments, the peptide has an amino acid sequence that is SEQ ID NO:7. In some embodiments, the peptide has an amino acid sequence that is SEQ ID NO:9.

Peptides useful in the present invention can have a molecular weight of at least 2 kDa and exhibit a tertiary structure. For example, the molecular weight of the peptide can be from about 2 kDa to about 150 kDa, from about 5 kDa to about 150 kDa, from about 5 kDa to about 100 kDa, from about 2 kDa to about 50 kDa, from about 5 kDa to about 50 kDa, from about 5 kDa to about 30 kDa, from about 10 kDa to about 30 kDa, or from about 10 kDa to about 20 kDa. Representative molecular weights for the peptide includes about 2 kDa, or 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, 100, 110, 120, 130, 140, or about 150 kDa.

Conjugates

The conjugates of the present invention can be described as compounds of Formula I:

$$(X\text{—}Y)_n\text{—}Z \tag{I}$$

where X is the peptide as described above, Z is the biocompatible polymer as described above, Y is an optional linker, and subscript n is from 5 to 500.

The peptide-polymer conjugates of the present invention can include any suitable combination of peptide and biocompatible polymer where the molar ratio of peptide to polymer is at least 5:1. Representative molar ratios of peptide to biocompatible polymer useful in the present invention include from 5:1 to about 1000:1, from 5:1 to about 500:1, from 5:1 to about 400:1, from about 10:1 to about 500:1, from about 10:1 to about 400:1, from about 10:1 to about 300:1, from about 10:1 to about 200:1, from about 10:1 to about 100:1, from about 20:1 to about 100:1, from about 30:1 to about 100:1, from about 50:1 to about 100:1, from about 10:1 to about 50:1, from about 20:1 to about 50:1, or from about 30:1 to about 50:1. Other molar ratios of peptide to biocompatible polymer useful in the present invention include from about 50:1 to about 500:1, from about 50:1 to about 400:1, from about 50:1 to about 300:1, or from about 50:1 to about 200:1. Representative molar ratios of peptide to biocompatible polymer include about 10:1, or 15:1, 20:1, 25:1, 30:1, 35:1, 40:1, 45:1, 50:1, 60:1, 70:1, 80:1, 90:1, 100:1, 125:1, 150:1, 175:1, 200:1, 250:1, 300:1, 350:1, 450:1 or about 500:1.

Each peptide can be linked to the biocompatible polymer by a variety of linkers generally known in the art for forming antibody-drug conjugates, such as those provided by BroadPharm of San Diego, Calif. Methods for forming bioconjugate bonds are described in Bioconjugate Techniques, 3rd Edition, Greg T. Hermanson. The linkers can be reactive with amines, carbonyls, carboxyl and activated esters, can react via Click-chemistry (with or without copper), or be reactive with thiols.

For example, the peptide can be linked covalently directly to the biocompatible polymer without any linker. Or the peptide can be linked to the biocompatible polymer by formation of an ionic bond such as via carboxylate and ammonium ions. When a linker is used to covalently link the peptide to the biocompatible polymer the linker, representative linkers include an amide or disulfide, or are formed from a reactive group such as succinic anhydride, succinimide, N-hydroxy succinimide, N-chlorosuccinimide, N-bromosuccinimide, maleic anhydride, maleimide, hydantoin, phthalimide, and others. The linkers useful in the present invention are small and generally have a molecular weight from about 100 Da to about 500 Da containing two functional groups consisting of a maleimide and either an amine or hydrazide. In some embodiments, the peptide is covalently linked to the polymer via a sulfide bond and a linker having a molecular weight of from about 100 Da to about 500 Da. In some embodiments, the linker has a molecular weight of from about 100 Da to about 300 Da. In some embodiments, the linker comprises a succinimide. In some embodiments, the linker is formed using N-beta-maleimidopropionic acid hydrazide (BMPH), N-epsilon-maleimidocaproic acid hydrazide (EMCH), N-aminoethyl-maleimide, N-kappa-maleimidoundecanoic acid hydrazide (KUMH), hydrazide-PEG2-maleimide, amine-PEG2-maleimide, hydrazide-PEG3-maleimide, or amine-PEG3-maleimide.

Representative linker groups Y in Formula I include, but are not limited to,

In some embodiments, the linker group Y can be N-epsilon-maleimidocaproic acid hydrazide (EMCH):

Linkers useful in the conjugates of the present invention can also be short peptides. A flexible, semiflexible, rigid peptide linker may be included as a part of the anti-inflammatory peptide sequence.

The conjugates of the peptide of biocompatible polymer of the present invention can have longer diffusion half-lives compared to the unconjugated peptide. For example, the conjugate can have a diffusion half-life of at least 2 times longer than that of the peptide, or 3, 4, 5, 6, 7, 8, 9, 10, 15, 20, 25, 30, 35, 40, 45, 50, 60, 70, 80, 90, or at least 100 times longer than that of the peptide. The diffusion half-life of the conjugate can be from about 2 to about 100 times longer than the peptide, or from about 2 to about 50, from about 10 to about 100, from about 25 to about 100, from about 50 to about 100 times longer than the peptide. In some embodiments, the diffusion half-life of the conjugate is at least about 2 times longer than the peptide. In some embodiments, the diffusion half-life of the conjugate is from about 2 to about 100 times longer than the peptide.

The conjugates of the present invention can also have longer intra-articular half-lives compared to the unconjugated peptide. For example, the conjugate can have an intra-articular half-life that is at least 20% longer than the unconjugated peptide, or at least 50, 75, 100, 150, 200, 250, 300, 350, 400, 450, 500, 600, 700, 800, 900 or 1000% longer than the unconjugated peptide. The intra-articular half-life of the conjugate can be from about 20% to about 1000% longer than the unconjugated peptide, or from about 100% to about 1000%, or from about 100% to about 500%, or from about 100% to about 300% longer than the unconjugated peptide. In some embodiments, the intra-articular half-life of the conjugate is at least about 20% longer than the peptide. In some embodiments, the intra-articular half-life of the conjugate is from about 20% to about 1000% longer than the peptide.

In some embodiments, the biocompatible polymer has a molecular weight of from about 0.8 MDa to about 3 MDa; and each peptide has a molecular weight of from about 5 kDa to about 50 kDa; wherein each peptide is covalently linked to the polymer, and the molar ratio of the peptides to the polymer in the conjugate is at least about 10:1. In some embodiments, the biocompatible polymer has a molecular weight of from about 0.8 MDa to about 2 MDa; and each peptide has a molecular weight of from about 5 kDa to about 50 kDa; wherein each peptide is covalently linked to the polymer, and the molar ratio of the peptides to the polymer in the conjugate is at least about 10:1. In some embodiments, the biocompatible polymer has a molecular weight of from about 1 MDa to about 2 MDa; and each peptide has a molecular weight of from about 5 kDa to about 50 kDa; wherein each peptide is covalently linked to the polymer, and the molar ratio of the peptides to the polymer in the conjugate is at least about 10:1. In some embodiments, the biocompatible polymer has a molecular weight of from about 1 MDa to about 2 MDa; and each peptide has a molecular weight of from about 5 kDa to about 50 kDa; wherein each peptide is covalently linked to the polymer, and the molar ratio of the peptides to the polymer in the conjugate is at least about 20:1. In some embodiments, the biocompatible polymer has a molecular weight of about 2 MDa; and each peptide has a molecular weight of from about 5 kDa to about 50 kDa; wherein each peptide is covalently linked to the polymer, and the molar ratio of the peptides to the polymer in the conjugate is at least about 50:1.

In some embodiments, the present invention provides a conjugate of (anti-TNF$\alpha$ VHH antibody-EMCH)$_{13}$-HyA (200 kDa), (anti-TNF$\alpha$ VHH antibody-EMCH)$_{17}$-HyA (350 kDa), (anti-TNF$\alpha$ VHH antibody-EMCH)$_{23}$-HyA (750 kDa), (anti-TNF$\alpha$ VHH antibody-EMCH)$_{46}$-HyA (850 kDa), (anti-TNF$\alpha$ VHH antibody-EMCH)$_{88}$-HyA (1350 kDa), (anti-TNF$\alpha$ VHH antibody-EMCH)$_{184}$-HyA (2000 kDa), (anti-(mouse)TNF$\alpha$ VHH antibody-EMCH)$_{273}$-HyA (2000 kDa), (anti-TNF$\alpha$ VHH antibody-EMCH)$_{41}$-CMC (90 kDa), (anti-TNF$\alpha$ VHH antibody-EMCH)$_{37}$-CMC (250 kDa), (anti-TNF$\alpha$ VHH antibody-EMCH)$_{42}$-CMC (700 kDa), (anti-TNF$\alpha$ VHH antibody-EMCH)$_5$-CM Chitosan (200 kDa), (anti-TNF$\alpha$ VHH antibody-EMCH)$_{13}$-HyA (200 kDa), (anti-TNF$\alpha$ affibody-EMCH)$_{21}$-HyA (850 kDa), (anti-TNF$\alpha$ affibody-EMCH)$_{22}$-CMC (700 kDa), (anti-IL-1$\beta$ scFv antibody-EMCH)$_{15}$-HyA (2000 kDa), or (anti-IL-1$\beta$ scFv antibody-EMCH)$_{13}$-CMC (700 kDa). In some embodiments, the present invention provides a conjugate of (anti-TNF$\alpha$ VHH antibody-EMCH)$_{13}$-HyA (200 kDa), (anti-TNF$\alpha$ VHH antibody-EMCH)$_{17}$-HyA (350 kDa), (anti-TNF$\alpha$ VHH antibody-EMCH)$_{23}$-HyA (750 kDa), (anti-TNF$\alpha$ VHH antibody-EMCH)$_{46}$-HyA (850 kDa), (anti-TNF$\alpha$ VHH antibody-EMCH)$_{88}$-HyA (1350 kDa), (anti-TNF$\alpha$ VHH antibody-EMCH)$_{184}$-HyA (2000 kDa), (anti-(mouse)TNF$\alpha$ VHH antibody-EMCH)$_{273}$-HyA (2000 kDa), (anti-TNF$\alpha$ VHH antibody-EMCH)$_{37}$-CMC (250 kDa), (anti-TNF$\alpha$ VHH antibody-EMCH)$_{42}$-CMC (700 kDa), (anti-TNF$\alpha$ VHH antibody-EMCH)$_5$-CM Chitosan (200 kDa), (anti-TNF$\alpha$ VHH antibody-EMCH)$_{13}$-HyA (200 kDa), (anti-TNF$\alpha$ affibody-EMCH)$_{21}$-HyA (850 kDa), (anti-TNF$\alpha$ affibody-EMCH)$_{22}$-CMC (700 kDa), (anti-IL-1$\beta$ scFv antibody-EMCH)$_{15}$-HyA (2000 kDa), or (anti-IL-1$\beta$ scFv antibody-EMCH)$_{13}$-CMC (700 kDa). In some embodiments, the present invention provides a conjugate of (anti-TNF$\alpha$ VHH antibody-EMCH)$_{46}$-HyA (850 kDa), (anti-TNF$\alpha$ VHH antibody-EMCH)$_{88}$-HyA (1350 kDa), (anti-TNF$\alpha$ VHH antibody-EMCH)$_{184}$-HyA (2000 kDa), (anti-(mouse)TNF$\alpha$ VHH antibody-EMCH)$_{273}$-HyA (2000 kDa), (anti-TNF$\alpha$ affibody-EMCH)$_{21}$-HyA (850 kDa), or (anti-IL-1$\beta$ scFv antibody-EMCH)$_{15}$-HyA (2000 kDa). In some embodiments, the present invention provides a conjugate of (anti-TNF$\alpha$ VHH antibody-EMCH)$_{46}$-HyA (850 kDa), (anti-TNF$\alpha$ VHH antibody-EMCH)$_{88}$-HyA (1350 kDa), (anti-TNF$\alpha$ VHH antibody-EMCH)$_{184}$-HyA (2000 kDa), (anti-(mouse)TNF$\alpha$ VHH antibody-EMCH)$_{273}$-HyA (2000 kDa), (anti-TNF$\alpha$ affibody-EMCH)$_{21}$-HyA (850 kDa), or (anti-IL-1$\beta$ scFv antibody-EMCH)$_{35}$-HyA (2000 kDa).

IV. Pharmaceutical Compositions

In some embodiments, the present invention provides a pharmaceutical composition including a conjugate of the present invention and a pharmaceutically acceptable excipient.

A. Formulation

For preparing pharmaceutical compositions from the conjugates of the present invention, pharmaceutically acceptable carriers can be either solid or liquid. Solid form preparations include powders, cachets, and dispersible granules. A solid carrier can be one or more substances, which may also act as diluents, binders, preservatives, disintegrating agents, or an encapsulating material. Details on techniques for formulation and administration are well described in the scientific and patent literature, see, e.g., the latest edition of Remington's Pharmaceutical Sciences, Maack Publishing Co, Easton Pa. ("Remington's").

In powders, the carrier is a finely divided solid, which is in a mixture with the finely divided active component. In tablets, the active component is mixed with the carrier having the necessary binding properties in suitable proportions and compacted in the shape and size desired. The powders and tablets preferably contain from 5% or 10% to 70% of the conjugates of the present invention.

Liquid form preparations include solutions, suspensions, and emulsions, for example, water or water/propylene glycol solutions. For parenteral injection, liquid preparations can be formulated in solution in aqueous polyethylene glycol solution.

Aqueous solutions suitable for oral use can be prepared by dissolving the conjugates of the present invention in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolality.

Also included are solid form preparations, which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

Oil suspensions can be formulated by suspending the conjugates of the present invention in a vegetable oil, such as arachis oil, olive oil, sesame oil or coconut oil, or in a mineral oil such as liquid paraffin; or a mixture of these. The oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto, J. Pharmacol. Exp. Ther. 281:93-102, 1997. The pharmaceutical formulations of the invention can also be in the form of oil-in-water emulsions. The oily phase can be a vegetable oil or a mineral oil, described above, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent.

The compositions of the present invention can also be delivered as microspheres for slow release in the body. For example, microspheres can be formulated for administration via intradermal injection of drug-containing microspheres, which slowly release subcutaneously (see Rao, J. Biomater Sci. Polym. Ed. 7:623-645, 1995; as biodegradable and injectable gel formulations (see, e.g., Gao Pharm. Res. 12:857-863, 1995); or, as microspheres for oral administration (see, e.g., Eyles, J. Pharm. Pharmacol. 49:669-674, 1997). Both transdermal and intradermal routes afford constant delivery for weeks or months.

In another embodiment, the compositions of the present invention can be formulated for parenteral administration into a body cavity such as the intra articular space of a joint. The formulations for administration will commonly comprise a solution of the compositions of the present invention dissolved in a pharmaceutically acceptable carrier. Among the acceptable vehicles and solvents that can be employed are water and Ringer's solution, an isotonic sodium chloride. In addition, sterile fixed oils can conventionally be employed as a solvent or suspending medium. For this purpose any bland fixed oil can be employed including synthetic mono- or diglycerides. In addition, fatty acids such as oleic acid can likewise be used in the preparation of injectables. These solutions are sterile and generally free of undesirable matter. These formulations may be sterilized by conventional, well known sterilization techniques. The formulations may contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of the compositions of the present invention in these formulations can vary widely, and will be selected primarily based on fluid volumes, viscosities, body weight, and the like, in accordance with the particular mode of administration selected and the patient's needs. For IV administration, the formulation can be a sterile injectable preparation, such as a sterile injectable aqueous or oleaginous suspension. This suspension can be formulated according to the known art using those suitable dispersing or wetting agents and suspending agents. The sterile injectable preparation can also be a sterile injectable solution or suspension in a nontoxic parenterally-acceptable diluent or solvent, such as a solution of 1,3-butanediol.

In another embodiment, the formulations of the compositions of the present invention can be delivered by the use of liposomes which fuse with the cellular membrane or are endocytosed, i.e., by employing ligands attached to the liposome, or attached directly to the oligonucleotide, that bind to surface membrane protein receptors of the cell resulting in endocytosis. By using liposomes, particularly where the liposome surface carries ligands specific for target cells, or are otherwise preferentially directed to a specific organ, one can focus the delivery of the compositions of the present invention into the target cells in vivo. (See, e.g., Al-Muhammed, J. Microencapsul. 13:293-306, 1996; Chonn, Curr. Opin. Biotechnol. 6:698-708, 1995; Ostro, Am. J. Hosp. Pharm. 46: 1576-1587, 1989).

Lipid-based drug delivery systems include lipid solutions, lipid emulsions, lipid dispersions, self-emulsifying drug delivery systems (SEDDS) and self-microemulsifying drug delivery systems (SMEDDS). In particular, SEDDS and SMEDDS are isotropic mixtures of lipids, surfactants and co-surfactants that can disperse spontaneously in aqueous media and form fine emulsions (SEDDS) or microemulsions (SMEDDS). Lipids useful in the formulations of the present invention include any natural or synthetic lipids including, but not limited to, sesame seed oil, olive oil, castor oil, peanut oil, fatty acid esters, glycerol esters, Labrafil®, Labrasol®, Cremophor®, Solutol®, Tween®, Capryol®, Capmul®, Captex®, and Peceol®.

B. Administration

The conjugates and compositions of the present invention can be delivered by any suitable means, including oral, parenteral and topical methods. In some embodiments, the delivery method is intra-articular.

The pharmaceutical preparation is preferably in unit dosage form. In such form the preparation is subdivided into unit doses containing appropriate quantities of the conjugates and compositions of the present invention. The unit dosage form can be a packaged preparation, the package containing discrete quantities of preparation, such as packeted tablets, capsules, and powders in vials or ampoules.

The conjugates and compositions of the present invention can be co-administered with other agents. Co-administration includes administering the conjugate or composition of the present invention within 0.5, 1, 2, 4, 6, 8, 10, 12, 16, 20, or 24 hours of the other agent. Co-administration also includes administering simultaneously, approximately simultaneously (e.g., within about 1, 5, 10, 15, 20, or 30 minutes of each other), or sequentially in any order. Moreover, the conjugates and compositions of the present invention can each be administered once a day, or two, three, or more times per day so as to provide the preferred dosage level per day.

In some embodiments, co-administration can be accomplished by co-formulation, i.e., preparing a single pharmaceutical composition including the conjugates and compositions of the present invention and any other agent. Alternatively, the various components can be formulated separately.

The conjugates and compositions of the present invention, and any other agents, can be present in any suitable amount, and can depend on various factors including, but not limited to, weight and age of the subject, state of the disease, etc. Suitable dosage ranges include from about 0.1 mg to about 10,000 mg, or about 1 mg to about 1000 mg, or about 10 mg to about 750 mg, or about 25 mg to about 500 mg, or about 50 mg to about 250 mg. Suitable dosages also include about 1 mg, 5, 10, 20, 30, 40, 50, 60, 70, 80, 90, 100, 200, 300, 400, 500, 600, 700, 800, 900 or 1000 mg. The composition can also contain other compatible therapeutic agents. The conjugates described herein can be used in combination with one another, with other active agents known to be useful in modulating a glucocorticoid receptor, or with adjunctive agents that may not be effective alone, but may contribute to the efficacy of the active agent.

V. Methods

The present invention provides a method of treating a disease or disorder in an articular joint using a peptide-polymer conjugate of the present invention. In some embodiments, the present invention provides a method of treating a disease or disorder in an articular joint, the method comprising injecting into the articular joint an effective amount of a conjugate comprising: a biocompatible polymer having a molecular weight of from about 0.1 MDa to about 3 MDa; and a plurality of peptides, wherein the peptide has a molecular weight of from about 5 kDa to about 150 kDa; wherein each peptide is covalently linked to the polymer, and the molar ratio of the peptide to the polymer in the conjugate is at least about 5:1. In some embodiments, the present invention provides a method of treating a disease or disorder in an articular joint, the method comprising injecting into the articular joint an effective amount of a conjugate comprising: a biocompatible polymer having a molecular weight of from about 0.1 MDa to about 2 MDa; and a plurality of peptides, wherein the peptide has a molecular weight of from about 5 kDa to about 100 kDa; wherein each peptide is covalently linked to the polymer, the molecular weight of the polymer is from about 5 kDa to about 50 kDa per peptide, and the molar ratio of the peptide to the polymer in the conjugate is at least about 5:1.

The present invention also provides methods of treating disease and disorders of the joint tissues using the conjugates of the present invention. Examples of diseases and disorders of the joint tissues include, but are not limited to rheumatoid arthritis, wear-related osteoarthritis, age-related osteoarthritis, post-traumatic osteoarthritis, psoriatic arthritis, and aseptic implant loosening, joint effusion, ankylosing spondylitis, bursitis, gout, reactive, arthritis, synovitis, and avascular necrosis. In some embodiments, the disease or disorder is rheumatoid arthritis, wear-related osteoarthritis, age-related osteoarthritis, post-traumatic osteoarthritis, psoriatic arthritis, and aseptic implant loosening, joint effusion, ankylosing spondylitis, bursitis, gout, reactive arthritis, synovitis, or avascular necrosis.

Many polypeptides are used as drugs to attenuate immune cell function have substantial utility in treating many joint disorders. Joint tissues are particularly susceptible to injury and disease because the typical cellular responses to these assaults, i.e., upregulating of inflammatory mediators, is also a signal to encourage catabolism of articular cartilage and resorption of the underlying bone tissues. Degeneration of the articular surfaces encourages the worsening of damage to the joint tissues and further up regulation of inflammatory mediators. Over time, these mechanisms generate a feed-forward loop that results in cumulative damage to the joint tissues.

Any joint of the human or animal body can be treated using the methods and conjugates of the present invention. Representative joints include, but are not limited to, fibrous joints, cartilaginous joints, synovial joints, facet joints, synarthrosis joints, amphiarthrosis joints, and diarthrosis joints. The joints can be simple joints having two articulation surfaces, a compound joint having three or more articulation surfaces, or complex joints having two or more articulation surfaces and an articular knee or meniscus. Anatomical joints that can be treated using the conjugates and methods of the present invention include, but are not limited to, hand joints including the fingers, elbow joints, wrist joints, shoulder joints, joints of the sternum and clavicle, vertebral joints, jaw and skull joints, pelvic and hip joints, knee joints, ankle joints and foot joints including the toes. The joints can also be classified as a plane joint, ball and socket joint, hinge joint, pivot joint, condyloid joint and saddle joint. The conjugates and methods of the present invention can be used to treat the tissues of the joint, including, but not limited to, connective tissue, cartilage, articulation surfaces, synovial cavities, meniscus, and others.

Examples of drugs that are designed to attenuate immune cell function include antibodies that can interfere with Tumor Necrosis Factor-α and IL-1β, IL-6, or interferon-γ. Other examples include selective antibody inhibitors of T cell and B cell function. These antibodies may be monoclonal IgG antibodies, IgG antibody fragments, single chain scFv antibodies, single-domain heavy-chain VHH antibodies, or engineered antibody-like scaffolds such as adnectins, affibodies, anticalins, DARPins, and engineered Kunitz-type inhibitors. Other examples also include receptor decoys of immunomodulatory cytokines such as Tumor Necrosis Factor-α and IL-1β, IL-6, or interferon-γ.

One common side effect of using anti-inflammatory drugs such as those listed above is a higher risk of infection.

Because they attenuate the body's immune responses, the immune system becomes impaired to fight bacteria, viruses, and parasites. Therefore, the benefits of systemic use of these drugs needs to be weighed carefully against the risks associated with systemic immune suppression. In the case of diseases where the whole body is affected by a hyperimmune disorder, such as rheumatoid arthritis, systemic use of immune attenuating drugs may be justified. However, for conditions effecting only one or a limited number of joints, the system risk of infection often does not justify the systemic use of these drugs.

As an alternative, intra-articular (IA) administration of immune modulating drugs has been proposed to prevent or inhibit the long-term effects of inflammation that are associated with osteoarthritis. However, these drugs are rapidly cleared out of the joint space and do not provide adequate duration of therapy after IA administration. After IA injection, the half-life of anti-inflammatory proteins in the synovium is short (<1.5 hours). This is evident from clinical studies where inflammation inhibitors, including infliximab and etanercept, have been administered by IA injection in humans for a variety of joint disorders. Some of these studies report a significant reduction in joint inflammation, but acknowledge that frequent (e.g. weekly) administration was required for a successful outcome. Thus, IA anti-inflammatory therapy using existing drugs would be limited by high costs and the inconvenience of frequent IA dosing. Clearly, methods to extend anti-inflammatory drug bioactivity within the synovial fluid are needed to enable this therapeutic approach for treating joint disorders.

The primary symptoms associated with joint disorders are pain, effusion, limited range of motion, and pathological remodeling of the joint anatomy. Efficacy for a treatment to treat joint disorders may include a reduction in pain as measured by a generalized assessment, such as the visual assessment score. Efficacy may also be determined based on an improved score using a system that is specific to a particular joint disorder, such as the WOMAC score for osteoarthritis, the ACR20 for rheumatoid arthritis, the Psoriatic Arthritis Quality of Life for psoriatic arthritis, or the SASSS for ankylosing spondylitis. Efficacy may also be measured using a functional output, such as an increase in pain free walking distance or an increase in the range of joint motion. Efficacy may also be measured based on radiographic evidence showing restoration of normal joint anatomy.

The conjugate can be administered at any suitable frequency or amount as discussed above. In some embodiments, the conjugate is injected into the articular joint no more than about once a month. In some embodiments, the conjugate is injected into the articular joint from about once a month to once every 6 months. In some embodiments, the conjugate is injected into the articular joint once every 2 months or once every 3 months.

A. Osteoarthritis

In 2015, an estimated 7.75 million Americans experienced symptoms of osteoarthritis (OA) that could be associated with a known joint injury. Post-traumatic OA (PTOA) accounts for at least 15% of all OA cases, although it is assumed many other OA diagnoses may also be related to a prior joint trauma. Due to a lack of disease modifying therapies, joint replacement surgery is often the only treatment option to eliminate the associated discomfort and restore mobility. However, PTOA is often diagnosed in younger patients, for whom joint replacement is not a viable option. Overall, the cost of treating these PTOA patients exceeds $4B in health care costs each year.

Short-term inhibition of injury-related inflammation will limit the long-term symptoms of PTOA. Many types of joint injury have been associated with PTOA, including dislocations, ligament tears, meniscal damage, and intra-articular fractures. Although the initial damage may be acute, the injury is sufficient to initiate a cascade of inflammatory mediators. The resulting chronic whole-joint inflammation can encourage catabolism of the articular cartilage, resulting in further tissue damage that accumulates over time and presents as PTOA. TNFα and IL-1β have well-known roles in mediating joint inflammation. These cytokines interact to promote destruction of cartilage, which occurs by both downregulating the expression of the cartilage matrix components and upregulating the expression of matrix metalloproteinases (MMPs). TNFα also stimulates osteoclast recruitment, and induces apoptosis of bone-forming osteoblasts in inflammatory environments, which contributes to the erosion of articular cartilage tissues. TNFα and IL-1β are compelling targets for mitigating the inflammatory response to joint injury. Inhibiting these key acute inflammatory cytokines in the joint environment has been proposed for early intervention to stall the progression of PTOA.

B. Inflammation Due to Immune Response to Intra-Articular Microparticles

Wear occurring between the articular surfaces of a joint can generate particles at the micron scale that drive joint inflammation and osteolysis. Wear particles may be generated due to abrasion between endogenous surfaces, such as ossified cartilage lesions, osteophytes (bone spurs), or exposed subchondral bone lesion. This type of wear particle generation occurs frequently in later stage of OA, resulting in severe joint pain and immobility. This additional inflammatory response accelerates the rate of joint tissue degeneration in OA.

Wear particles may also be formed between the surfaces of an artificial joint. In 2015, more than 7 million Americans were living with an implanted artificial joint. Nearly 250,000 of these individuals will eventually require a revision surgery due to osteolysis of the bone surrounding the device, eventually resulting in device loosening and failure.

Wear-related inflammation stems from the foreign body response to otherwise inert microparticles shed from the articulating surfaces. Macrophages inside the synovial lining readily recognize wear microparticles as foreign bodies, release pro-inflammatory factors that recruit other active immune cells to the synovium, and stimulate osteoclast expansion while simultaneously inhibiting bone formation. Thus, sustained inflammation triggers a feed-forward cycle where cartilage degeneration and osteolysis leads to more abrasions between articulating surfaces and more movement and physical stress that in turn produces more particles.

In some embodiments, the peptide modulates the activity of immune cell function. In some embodiments, the peptide inhibits tumor necrosis factor-α, interleukin-1β, interleukin-6, or interferon-γ. In some embodiments, the peptide inhibits tumor necrosis factor-α.

Tumor necrosis factor (TNFα) is a compelling target for controlling the foreign body response. TNFα has a well-known role in mediating joint inflammation. TNFα also stimulates osteoclast recruitment, and induces apoptosis of bone-forming osteoblasts in inflammatory environments, leading to osteolysis of subchondral bone. Inhibition of TNFα using a systemically-administered receptor antagonist (etanercept) has been shown to reduce bone resorption induced by wear particles in mice, although the risks associated with systemic anti-TNFα are not generally regarded as acceptable for localized conditions. As an alternative, IA anti-TNFα therapy has been proposed to prevent or inhibit the osteolytic response to intra-articular wear particle In some embodiments, the peptide is a monoclonal IgG antibody, an IgG antibody fragment, a single-chain variable region antibody, a single-domain heavy chain antibody, an adnectin, an affibody, an anticalin, a DARPin, a Kunitz-type inhibitor, or a receptor decoy.

The methods of the present invention include a peptide-polymer conjugate comprising a biocompatible polymer having a molecular weight of from about 0.1 MDa to about 2 MDa; and a plurality of peptides each having a molecular weight of from about 5 kDa to about 100 kDa, wherein each peptide is covalently linked to the polymer, wherein there is from about 50 kDa of polymer to about 5 kDa of polymer for every peptide, and wherein the molar ratio of peptides to polymer is at least 5:1.

In some embodiments, the conjugate comprises a peptide having the CDRs according to SEQ ID NO:3 to SEQ ID NO:5:

```
                                    (SEQ ID NO: 3)
        DHSGYTYTIG, (SEQ ID NO: 4)
        ARIYWSSGNTYYADSVKG,
        and (SEQ ID NO: 5)
        RDGIPT.
```

In some embodiments, the conjugate comprises a peptide having an amino acid sequence according to SEQ ID NO:1:

```
                                    (SEQ ID NO: 1)
QVQLQESGGGLVQPGGSLRLSCAASGRTFSDHSGYTYTIGWFRQAPGKER

EFVARIYWSSGNTYYADSVKGRFAISRDIAKNTVDLTMNNLEPEDTAVYY

CAARDGIPTSRSVESYNYWGQGTQVTVSS.
```

In some embodiments, the conjugate comprises a peptide having an amino acid sequence according to SEQ ID NO:2:

```
                                    (SEQ ID NO: 2)
SNAQVQLQESGGGLVQPGGSLRLSCAASGRTFSDHSGYTYTIGWFRQAPG

KEREFVARIYWSSGNTYYADSVKGRFAISRDIAKNTVDLTMNNLEPEDTA

VYYCAARDGIPTSRSVESYNYWGQGTQVTVSSSPSTPPTPSPSTPPGGC.
```

The conjugates of the present invention are well-positioned to ameliorate inflammation that occurs near joint to inhibit subsequent cartilage degeneration and osteolysis. These conjugates have been designed to exhibit biophysical attributes that are matched to the macromolecules of the synovial fluid that is retained within the joint. In addition, conjugating multiple copies or the bioactive polypeptide is sufficient to increase their potency by engaging multivalent interactions with their targets. Thus, this invention is well suited to enable methods of administering long-acting drugs locally to articulating joints for the treatment of various diseases.

One example target market for bioconjugates drugs is the ~25% patients of patients who experience chronic inflammation and effusion following joint injury and are thus at risk for developing PTOA. Options for these patients are currently limited to systemic analgesia and local corticosteroid treatment. Failure to resolve the prolonged inflammatory phase can lead to catabolism of articular cartilage and result in further injury that accumulates over time. A treatment based on anti-inflammatory bioconjugates and designed for administration every three months (or even less frequently) could mitigate the effect of long-term joint inflammation, thereby reducing pain and delaying or preventing the need for costly surgeries. These benefits would likely outweigh the downsides of repeated IA injections (as many as 4 per year), which may include risk of infection, inconvenience for the patient, and procedure costs.

Another example target market for bioconjugates drugs are patients who experience chronic inflammation and pain due to the development of calcified cartilage lesions, bone spurs, or subchondral bone lesions. Although surgical repair may eliminate the acute cause of the pain, existing inflammation, inflammation due to surgery, and inflammation to additional wear particles will accelerate joint damage and degeneration. Long-term options for these patients are currently limited to systemic analgesia and local corticosteroid treatment. Failure to resolve the prolonged inflammatory phase can lead to failure of the articulating surface, which requires joint replacement surgery to return the patient back to physical activity. A treatment based on anti-inflammatory bioconjugates and designed for administration every three months (or even less frequently) could mitigate the effect of long-term joint inflammation, thereby reducing pain and delaying or preventing the need for costly surgeries. These benefits would likely outweigh the downsides of repeated IA injections (as many as 4 per year), which may include risk of infection, inconvenience for the patient, and procedure costs.

Another example target market for bioconjugates drugs is the ~25% of patients with artificial joints who experience pain and effusion following joint replacement but do not demonstrate evidence of peri-implant infection to account for these symptoms. Options for these patients are currently limited to analgesia and clinical monitoring until subsequent osteolysis leads to device failure. A treatment based on anti-inflammatory bioconjugates designed for administration every three months or less frequent administration could mitigate the response to wear particles, thereby reducing pain and delaying or preventing the need for costly revision surgeries. These benefits would likely outweigh the downsides of chronic IA injections (as many as 4 per year), which may include risk of infection, inconvenience for the patient, and procedure costs.

Multivalent antibody conjugates are well-positioned to ameliorate inflammation that occurs due to joint injury or exposure to wear particles and inhibit the subsequent catabolic tissue damage. In addition to exhibiting high potency, the conjugates can be engineered with specific macromolecular properties will be retained within the joint. By conjugating an anti-inflammatory peptide to HyA that is sufficiently large to be retained with the synovium, the bioactive half-life of the conjugated antibody may be significantly extended compared to equivalent unconjugated antibodies.

VI. Examples

Example 1. Preparation of Conjugates

General Method.

Anti-inflammatory bioconjugates were prepared following a method described previously (PMID: 28679037). Polymers over a range of MWs from 150 kDa-2.0 MDa, were obtained which are referred to here based on their weight averaged MW, as specified from the manufacturer.

The polymers were put into a solution using an aqueous solution that include 0.1-1M of an appropriate buffer to maintain the pH in the range of 5.5-8.5, for example MES, Phosphate Buffer, His Buffer, MOPS, Glucuronic Acid, Citrate, Acetate HEPES.

One or more of the following excipients was added to the solution to encourage the polymers into solution: 50-500 mM NaCl, 0.0001-0.1% Tween-20, 0.0001-0.1% Tween-80, 1-10% sucrose, 1-10% manose, 1-10% trehalose, 1-10%, 1-10% mannitol, 1-10% sorbitol, 1-10% glycerol, etc. One or more of the following methods of agitation were used to encourage them to go into solution: rocking, orbital shaking, rotation, or stirring (e.g., with a stir bar or vertical stirrer).

A carbodiimide substitution of the carboxylic acid side groups on the polymers was initiated to generate a conjugation handle for the anti-inflammatory peptides. For each 3 mg of polymer, were added the following to the solution: 1-10 mg/mL 1-ethyl-3-(3-dimethylaminopropyl)carbodiimide hydrochloride (EDC) one of the following: 0.25-2.5 mg/mL N-ε-maleimidocaproic acid hydrazide (EMCH), 0.25-2.5 mg/mL BMPH, 0.25-2.5 mg/mL hydrazide-PEG2-maleimide, or 0.25-2.5 mg/mL amine-PEG2-maleimide. One of the following was added to facilitate the carbodiimide reaction: 0.1-3 mg/mL sulfo-NHS, 0.1-3 mg/mL Oxyma, or 0.01-0.1 mg/mL HOBt. The solution was allowed to react for 2 hours at either 4 degrees C. or at ambient temperatures. Unreacted conjugation reactions remove by were dialyzed with 50 kDa MWCO membranes against one of the buffer solutions listed. The dialysis buffer were changed after 4 hours twice and then once after 24 hours. The product of this reaction was polymer with the addition of maleimide reactive groups at 0.5-5% of the available carboxylic acid reactive groups.

The maleimide-activated polymers were then reacted with anti-inflammatory peptides. Acceptable targets to inhibit inflammation and peptide moieties are listed elsewhere in the specification). Peptides were engineered to include a cysteine available for conjugation at either the C-terminus or the N-terminus. A flexible, semiflexible, rigid peptide linker may be included as a part of the anti-inflammatory peptide sequence. Additional peptides may also be added to the anti-inflammatory peptide sequence to facilitate peptide purification, such as HIS6, FLAG or Streptavidin, which may or may not be cleaved prior to conjugation. The peptides were generated using an appropriate recombinant expression system, such as *E. coli*, yeast, CHO cells, tobacco leaf, etc.

To obtain Anti-Inflammatory bioconjugates with peptides conjugated over a range of valencies, a fixed concentration of peptide was combined with the polymer at various defined feed ratios in PBS and allowed to react at either 4 degrees C. or ambient temperature for 4 hours. During the conjugation reaction, one or more of the following was added to improve the reaction efficiency: 0.5-5 mM TCEP to minimize disulfide bringing between peptides and/or 0.5-5 mM EDTA to minimize free thiol oxidation. Unreacted peptide was removed from the peptide-polymer conjugates by one or more of the following methods: dialysis with 50-100 kDa MWCO against one of the buffers listed above twice for 4 hours and once for 24 hours at 4° C., tangential flow filtration against one of the buffers listed above, FPLC polishing using a size exclusion column, FPLC polishing with an affinity chromatography column designed to bind the polymer component of the conjugate, or ethanol precipitation of the conjugates.

Preparation of all exemplary conjugates described in Table 1 were synthesized using the following method (FIG.

1). First, a 4 mg/mL solution of each biopolymer was prepared in a MES Buffer (0.1 M, pH 5.7) and the solution was allowed to agitate for 24 hours by rotation (~5 RPM) at ambient temperature to ensure the polymer was fully in solution. For each 4 mg of polymer, were added the following to the solution: 8.8 mg/mL 1-ethyl-3-(3-dimethylamino-propyl)carbodiimide hydrochloride (EDC), 0.8 mg/mL N-ε-maleimidocaproic acid hydrazide (EMCH), and 0.04 mg/mL HOBt. The solution was allowed to react for 2 hours while agitating by rotation (~5 RPM) at ambient temperatures. Unreacted conjugation reagents were removed by were removed by dialysis using 50 kDa MWCO membranes against each of the following buffer solutions in sequence: First, Phosphate buffered saline (pH 6.5) with 50 mM Glycine added for 4 hours, second phosphate buffered saline (pH 6.5) overnight, and third, phosphate buffered saline (pH 6.5) with 10% glycerol added for 4 hours. To each solution of EMCH-activated polymer, the peptide was added at a 60:1 peptide:polymer molar feed ratio and Tween-20 to a final concentration of 0.01%. The solution was allowed to react for 2 hours while agitating by rotation (~5 RPM) at ambient temperatures. Unreacted peptides were removed by were removed by dialysis using 100 kDa MWCO membranes against each of the following buffer solutions in sequence: First, phosphate buffered saline (pH 7) with 0.01% Tween-20 for 4 hours, second phosphate buffered saline (pH 7) with 0.01% Tween-20 overnight, and phosphate buffered saline (pH 7) with 0.01% Tween-20 for 4 hours.

Example 2. Characterization of Conjugates

A variety of methods were used to evaluate the compositions of matter that are suitable in the disclosed treatment method for individuals with an inflammatory joint disease or disorder. The concentration of the peptide content in the conjugation reactions was determined using standard methods for protein concentration, such as BCA, Bradford, and/or UV absorption at A280. The concentration of the polymer content in the conjugation reactions was determined using UV absorption at A204. The concentration of the polymer content can also be measured by digestion with sulphuric acid followed by incubation with phenol to derive a product that can be analyzed by colorimetric analysis and compared against a standard curve. The concentrations of the peptide and the polymer may also be analyzed by mass spectrometry analysis following complete depolymerization of the polymer component by either enzymatic or acid digestion. The molar ratio of the polymers to peptides, as determined from the concentration measurements, were used to estimate the valency of each conjugate.

Covalent chemical conjugation between the peptides and the polymers was confirmed by running the products of the reaction on an SDS-PAGE gel under reducing and non-reducing conditions. These methods are sufficient to determine whether the product of the conjugation reaction contains any unconjugated peptide or peptides that have reacted with the polymer at a labile, off-target reaction site. The gels may be stained using a Coomassie blue stain a or a higher resolution SYPRO ruby stain. Conjugated protein will remain near the top of the loading wells, whereas unconjugated or labile-bound peptide will travel through the gel as anticipated based on their molecular weight. By this method, it is possible to make a rough approximation of unconjugated peptide down to approximately 0.1% of the total concentration of the peptide that was detected in the conjugation reaction product. Alternatively, it was possible to pass the conjugation reaction product through a size exclusion column (SEC) using an HPLC to separate and quantify the conjugated peptide from the unconjugated peptide. This method will also provide a rough estimate for the size of the peptide-polymer conjugates.

Light scattering methods were used to calculate the size of the peptide-polymer conjugates. For example, static multi-angle laser light scattering (MALLS) methods were used on the conjugation product after separation by SEC to determine the number and weight averaged molecular weights of the peptide-polymer conjugates. Further, by also measuring the absorptivity refractivity of the size-separated conjugates using an in-line UV detector and differential refractometer, the proportion of the conjugates was estimated that were consisting of either the peptide or polymer component. Thus SEC-MALLS analysis could provide an independent estimate of the peptide valency (i.e., ratio of peptides per polymer) as well as an estimate of the final number average and weight averaged molecular weight of the conjugated polymer. The SEC-MALLS analysis will also yield the mean radius of gyration (Rg) and the distribution of Rg for the conjugates. Dynamic light scattering was used to estimate the mean hydrodynamic radius (Rh) and the distribution of Rh for the conjugates.

TABLE 1

| | | Conjugates | | |
|---|---|---|---|---|
| Entry | Peptide | Linker | Polymer (MW) | Ratio of Peptide:Polymer |
| 1 | anti-TNFα VHH antibody (SEQ ID NO: 7) | EMCH | HyA (200 kDa) | 13 |
| 2 | anti-TNFα VHH antibody (SEQ ID NO: 7) | EMCH | HyA (350 kDa) | 17 |
| 3 | anti-TNFα VHH antibody (SEQ ID NO: 7) | EMCH | HyA (750 kDa) | 23 |
| 4 | anti-TNFα VHH antibody (SEQ ID NO: 7) | EMCH | HyA (850 kDa) | 46 |
| 5 | anti-TNFα VHH antibody (SEQ ID NO: 7) | EMCH | HyA (1350 kDa) | 88 |
| 6 | anti-TNFα VHH antibody (SEQ ID NO: 7) | EMCH | HyA (2000 kDa) | 184 |
| 7 | anti-(mouse) TNFα VHH (SEQ ID NO: 11) | EMCH | HyA (2000 kDa) | 273 |
| 8 | anti-TNFα VHH antibody (SEQ ID NO: 7) | EMCH | CMC (90 kDa) | 41 |
| 9 | anti-TNFα VHH antibody (SEQ ID NO: 7) | EMCH | CMC (250 kDa) | 37 |
| 10 | anti-TNFα VHH antibody (SEQ ID NO: 7) | EMCH | CMC (700 kDa) | 42 |
| 11 | anti-TNFα VHH antibody (SEQ ID NO: 7) | EMCH | CM Chitosan (200 kDa) | 5 |
| 12 | anti-TNFα affibody (SEQ ID NO: 6) | EMCH | HyA (850 kDa) | 21 |
| 13 | anti-TNFα affibody (SEQ ID NO: 6) | EMCH | CMC (700 kDa) | 22 |
| 14 | anti-IL-1β scFv antibody (SEQ ID NO: 9) | EMCH | HyA (2000 kDa) | 15 |
| 15 | anti-IL-1β scFv antibody (SEQ ID NO: 9) | EMCH | CMC (700 kDa) | 15 |

To verify that the peptides in each sample were covalently conjugated to the biopolymer backbones, the products of the conjugation reactions were analyzed with SDS-PAGE (Mini Protean System, BioRad) using 12% acrylamide gels run under reducing conditions by the addition of 2.5% beta mercaptoethanol. These conditions are able to separate peptide interactions due to non-covalent bonds. The peptides were visualized in the gels using SYPRO ruby (BioRad). Unconjugated peptides migrated through the gels as anticipated based on the peptide reference ladders, whereas the primary protein band for each bioconjugate was too large to enter the resolving gel. Only trace amounts of unconjugated peptide (less than 2% of the total peptide per sample) appeared as bands in the bioconjugate lanes. Thus, the peptides had been covalently conjugated to the biopolymer backbone each bioconjugate tested.

Figure 3A:
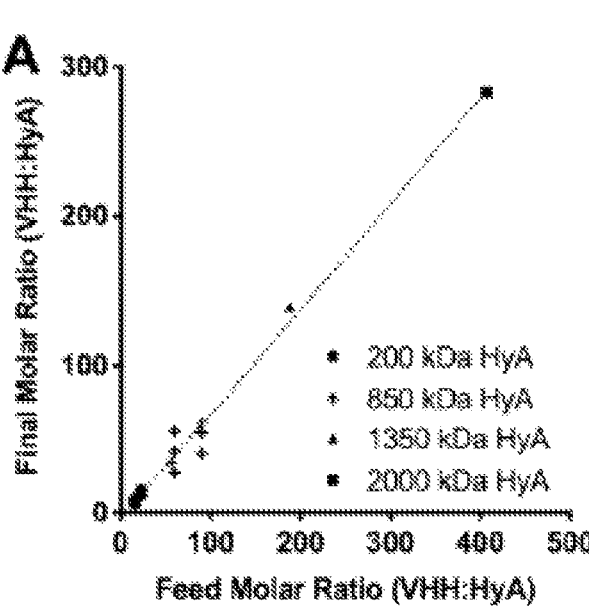
FIG. 3A shows characterization of multivalent conjugates to demonstrate anti-inflammatory peptide valency for various biopolymers based on the peptide feed ratio. In this example, VHH conjugation efficiency was 62±10% and independent of HyA molecular weight.
Figure 3B:
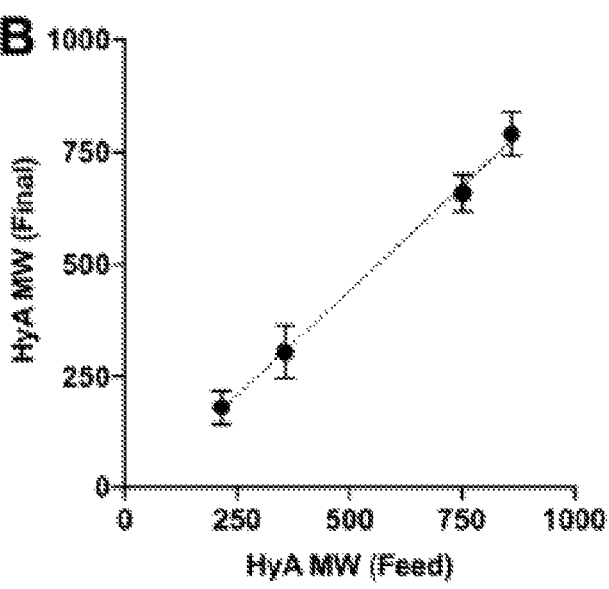
FIG. 3B shows the final distribution of the HyA component of the bioconjugates after the conjugation reactions.
Figure 3C:
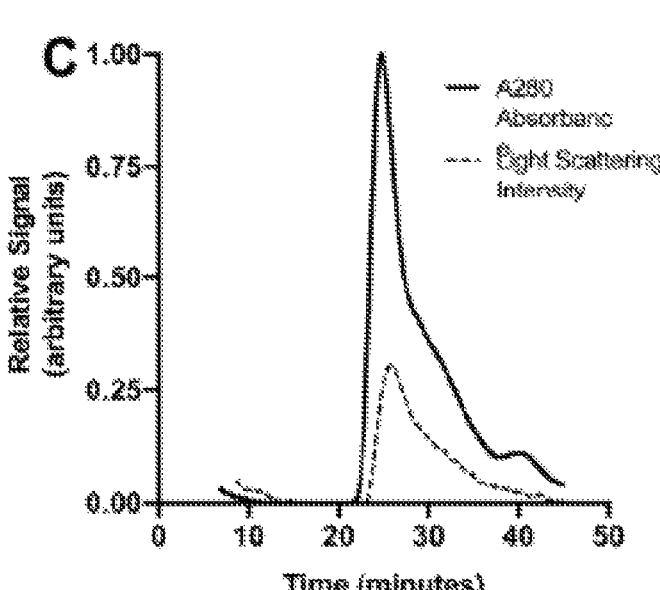
FIG. 3C shows example UV absorption and static light scattering chromatograms of anti-inflammatory bioconjugates after separation using a size exclusion column.
Figure 3D:
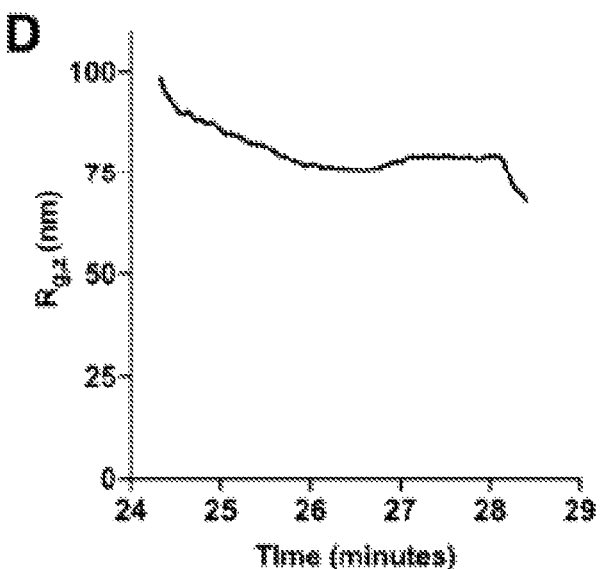
FIG. 3D shows the radius of gyration ($R_{g,z}$) for anti-inflammatory bioconjugates, as determined by static light scattering analysis, over the peak of the chromatogram shown in FIG. 3D.

Peptide molecular weight (FIG. 3A), HyA MW (FIG. 3B), size-exclusion chromatograms (FIG. 3C), and radius of gyration ($R_{g,z}$) were measured using established methods for size exclusion chromatography multi-angle light scattering (SEC-MALS; Bioconjug Chem. 2012; 23(9):1794). A branching analysis method was also used that assumes protein branches from a linear biopolymer to more accurately calculate the distribution of protein valencies over a range of HyA MW (Biomacromolecules. 2016; 17(10):3162). Based on previous experiments, empirical data can be used to predict the necessary feed ratios to achieve the target conjugate valency.

Example 3. Bioactivity of Anti-Inflammatory Bioconjugates

One or more of the following methods was used to measure the bioactivity of protein-polymer conjugates. As one example, BioLayer interferometry (BLI; ForteBio Octet Red) was used to determine the binding affinity of each peptide and peptide-polymer conjugate to their target. For this assay, the peptide targets are adsorbed onto a glass BLI probe. Most commonly targets that have either conjugated with biotin or expressed as a fusion peptide containing biotin are used to adsorb them to a BLI probe that has been pre-treated with a covalently-bound streptavidin surface layer. The probe adsorbed with the targets are then placed in a solution of either peptide or peptide-polymer conjugate that is at a known concentration. A laser light is then passed down the length of the BLI probe, and the laser light interference generated by peptide or conjugate binding to its target at the probe tip can be correlated directly to the mass of peptide or conjugate that has bound. The interference data over time can be used to calculate the k-on binding kinetics. By then placing the probe in a solution that does not contain any of the peptide or conjugate, the laser-light interference will reverse, the kinetics of which can be used to determine the k-off. Thus, this BLI method is capable of measuring the binding affinity (kD) of each peptide and conjugate to its target.

Figure 4A:
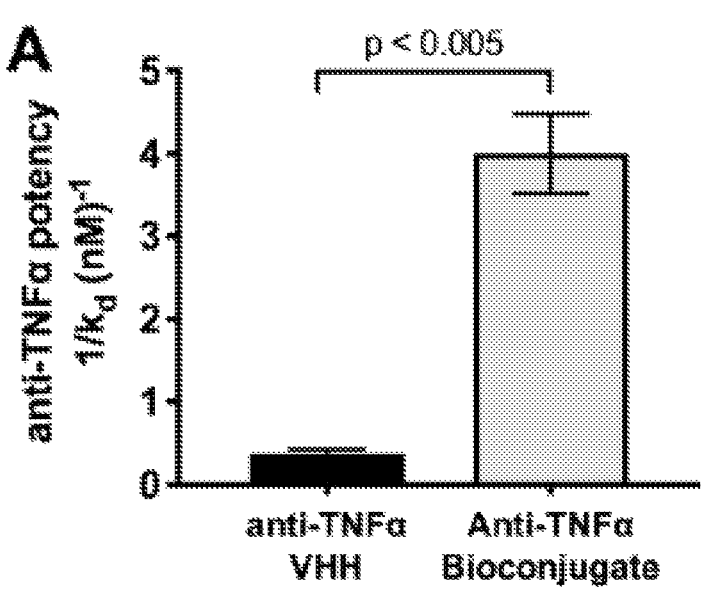
FIG. 4A shows that the TNFα binding affinity of an anti-TNFα VHH (SEQ ID NO:7)+HyA (850 kDa) bioconjugate is greater than that of an unconjugated anti-TNFα VHH antibody, as determined by biolayer interferometry (ForteBio Octet, Student's t-tests with n=3).

Multivalent presentation of anti-inflammatory antibodies is sufficient to enhance potency. As one example, anti-TNFα proteins were generated using published sequences for single-domain (VHH) camelid antibodies reactive to human TNFα (IC50=20 nM which are comparable to existing TNF inhibitors (e.g., infliximab: IC50=12 nM; Ann Rheum Dis. 2010; 69(2):443). These antibodies were conjugated to HyA to generate Anti-TNF bioconjugates on different MW HyA backbones (200 and 850 kDa) and then assessed bioactivity using BioLayer interferometry (BLI; ForteBio Octet Red) by adsorbing TNFα at a fixed concentration to the probe and measuring the binding affinity of anti-TNFα antibodies or Anti-TNF bioconjugates over a range of antibody/conjugate concentrations (FIG. 4A). After multivalent conjugation of anti-TNFα to either MW HyA backbones, the Anti-TNF bioconjugates exhibited higher potency to bind TNFα compared to unconjugated antibody. Additional bioactivity data is provided in Table 2.

TABLE 2

| Bioactivity Data | | |
| --- | --- | --- |
| | Bioactivity | |
| Table 1 Entry | $K_d$ (nM) | IC50 (nM) |
| 1 | 0.18 ± .07 | 32.5 ± 6.5 |
| 4 | 0.25 ± .03 | 54.0 ± 21.0 |
| 6 | 11.8 ± 16.6 | |
| 7 | 0.17 ± 0.9 | 120.5 ± 52.3 |
| 11 | 0.01 | |
| 12 | 0.02 | |
| 13 | 0.36 | |
| 14 | 0.84 ± 0.68 | |
| 15 | 0.02 ± 0.01 | |

Figure 4B:
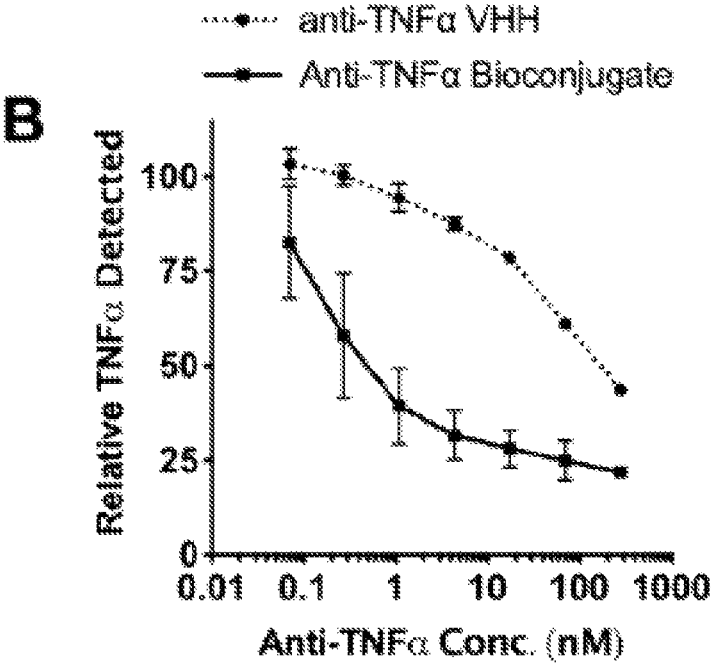
FIG. 4B shows compares the ability of an anti-TNFα VHH (SEQ ID NO:7)+HyA (850 kDa) bioconjugate and unconjugated anti-TNFα VHH to bind TNFα in solution using competitive ELISA (n=5).

Alternatively a competitive ELISA assay was used to verify the binding affinity of each peptide and peptide-polymer conjugate against its target (FIG. 4B). For this assay, a sandwich ELISA system was used that is designed to detect the peptide target to a low detection limit. Prior to beginning the assay, incubate each peptide or conjugate over a range of concentrations (e.g. 50-0.005 ng/mL) with the target peptide at a fixed concentration (e.g. 0.5 ng/mL). Target peptides that have been bound by the anti-inflammatory peptides or conjugates cannot be sandwiched by the ELISA antibodies to be detected by the ELISA, and thus this assay provides an independent verification of peptide and conjugate bioactivity, as well as a means of comparing the relative binding activities of the peptides and conjugates.

Figure 4C:
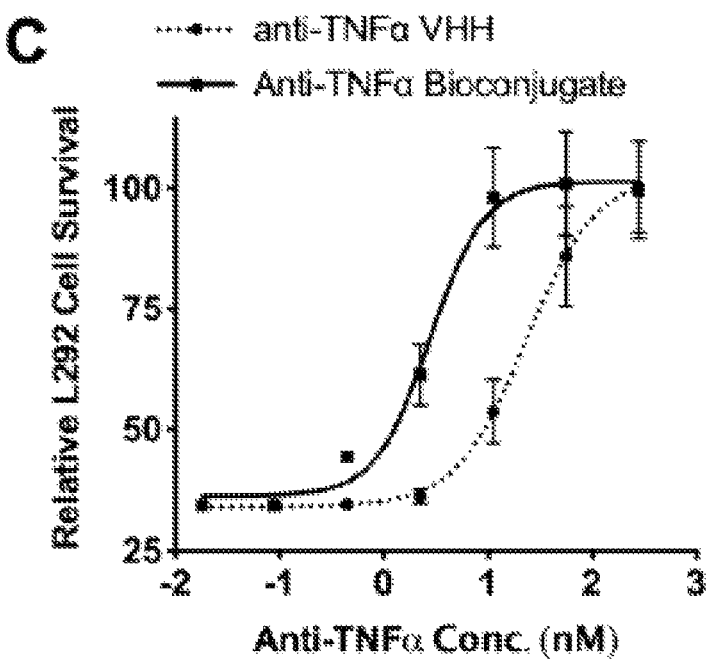
FIG. 4C compares the bioactivity of an anti-TNFα VHH (SEQ ID NO:7)+HyA (850 kDa) bioconjugate and unconjugated anti TNFα VHH in a bioassay to inhibit TNFα-induced apoptosis in L929 fibroblasts.
Figure 4D:
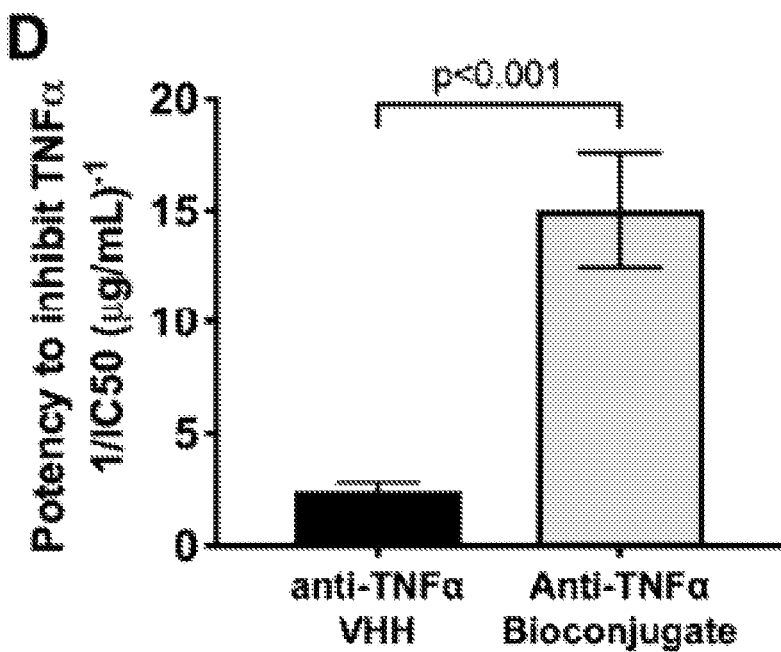
FIG. 4D shows that the potency of the anti-TNFα VHH+HyA bioconjugate was ~10 fold greater than the unconjugated VHH antibody based on the IC50s calculated from the fit of the FIG. 4C data (Student's t-tests with n=4).

Finally, the bioactivity of the anti-inflammatory peptides and peptide-polymer conjugates were quantified using cell-based pharmacology assays. For example, a cell survival assay based using L929 fibroblasts can be used to test the bioactivity of anti-inflammatory peptides that act by blocking the singling activity of TNFα (FIG. 4C). For this assay, the cells were treated with a TNFα at a fixed concentration (50 ng/mL) and the TNFα peptide inhibitor or the TNFα peptide-polymer conjugate inhibitor over a range of peptide concentrations (e.g. 500-0.05 ng/mL), and then assessed for cell survival after 24-72 hours. Methods of detecting for cell survival could include a standard assay for cell apoptosis, such as TUNEL, Actinomycin D, Caspase detection, etc. Cell survival may also be detected by comparing the relative growth rates from cell populations exposed to different concentrations of the TNFα inhibitors. The IC50 of each treatment can be calculated by fitting this data to a 4-parameter logistic fit (FIG. 4D)

Figure 2C:
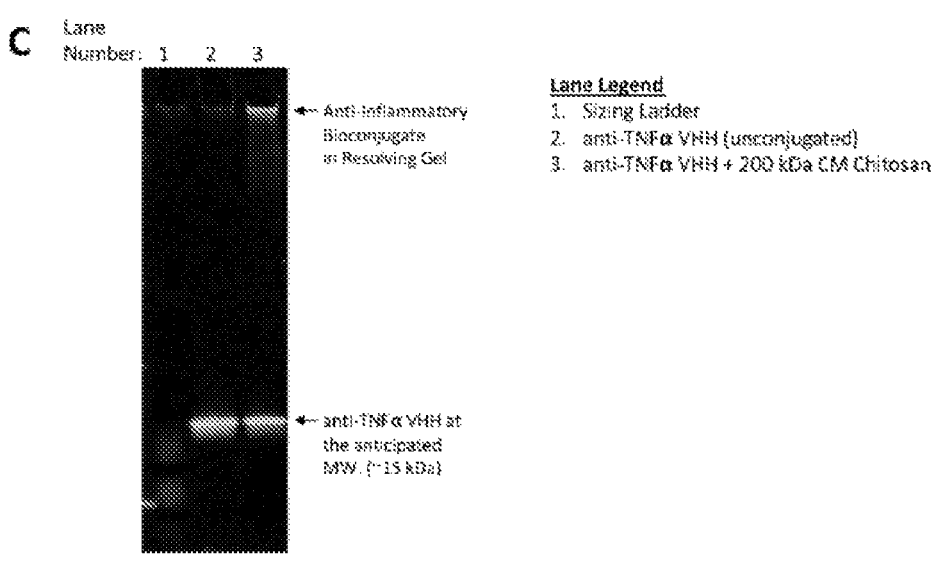
FIG. 2C shows an SDS-PAGE gel that was used to verify covalent binding between an anti-inflammatory anti-TNFα VHH antibody (SEQ ID NO:7) to CM Chitosan.
Figure 2D:
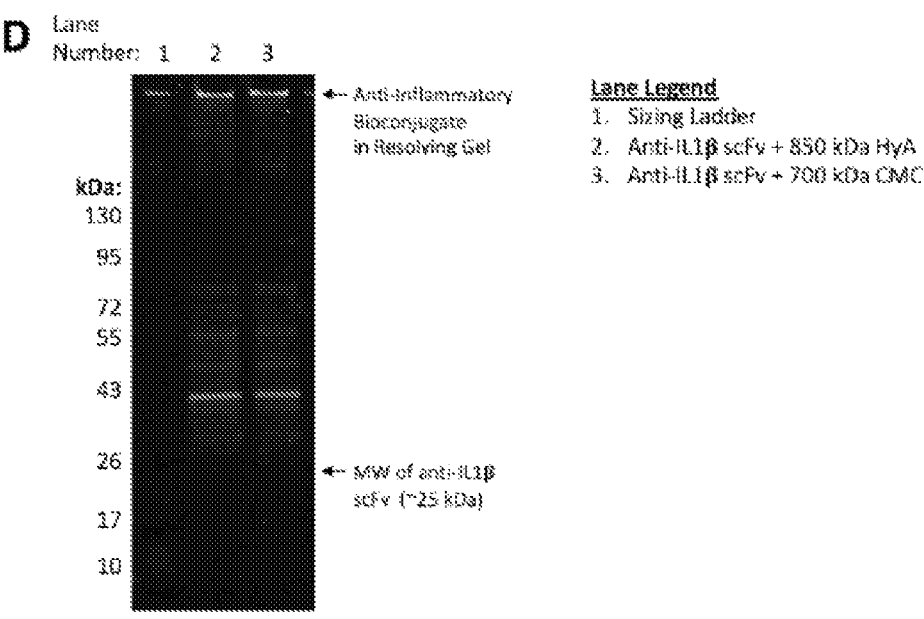
FIG. 2D shows an SDS-PAGE gel that was used to verify covalent binding of an anti-inflammatory anti-IL-1β scFv (SEQ ID NO:9) antibody to HyA and CMC.
Figure 2E:
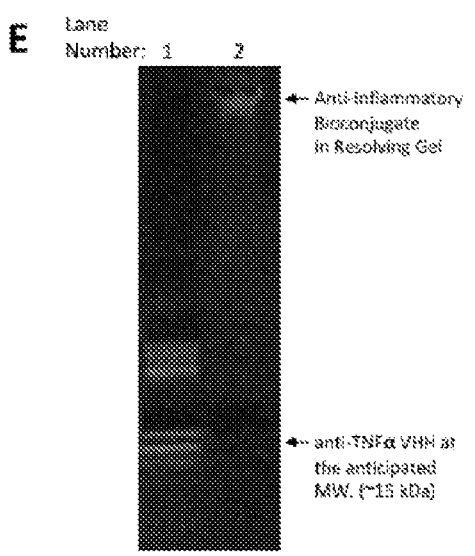
FIG. 2E shows an SDS-PAGE gel that was used to verify covalent binding of an anti-inflammatory anti-TNFα VHH (SEQ ID NO:7) antibody to CMC.

As a second example, a cell proliferation assay based using D10 lymphocytes can be used to test the bioactivity of anti-inflammatory peptides that act by blocking the singling activity of IL-1β. For this assay, the cells were treated with IL-1β at a fixed concentration (1 ng/mL) and the IL-1β peptide inhibitor or the IL-1β peptide-polymer conjugate inhibitor over a range of peptide concentrations (e.g. 100-0.01 ng/mL), and then assessed for cell proliferation after 24-72 hours (FIG. 2B). Methods of detecting for cell survival could include a standard assay for cell quantification, such as CyQuant, cell counting, or flow cytometry.

Example 4. Diffusion of Anti-Inflammatory Bioconjugates Across a Fenestrated Membrane Multivalent conjugate exhibit slower diffusivity across fenestrated membranes. The synovial fluid contains high molecular weight macromolecules that are retained within the joint space by a membrane of glycosaminoglycan molecules. This membrane contains fenestrations that allow the passage of small molecules and proteins out of the joint space, but retains the macromolecules.

The rate at which the peptide-polymer conjugate pass through a fenestrated membrane was measured using a benchtop assay. In these experiments, cylindrical chambers were obtained that were approximately 1 mL in volume and constructed from a membrane having fenestrations with mean diameters in a range from ~10-100 nm. The chambers were filled with solutions containing a known concentration of either the anti-inflammatory peptides or the protein-polymer, and the placed the membranes in a reservoirs of buffer solution that were at least 200 mL. These reservoirs were agitated by a stir bar to encourage transport of the peptides or conjugates across the membrane. Every 24 hours, for up to seven days, samples were taken from the solution inside the reservoir, and the peptide concentration was measured using a typical method of protein quantification, such as BCA, Bradford, or UV absorption at A260. The mass of the peptides inside the chambers fell at a rate that was consistent with a one-phase exponential decay. Therefore, the peptide concentrations were used to estimate the half-life of each peptide or conjugate within the chambers.

Figure 5A:
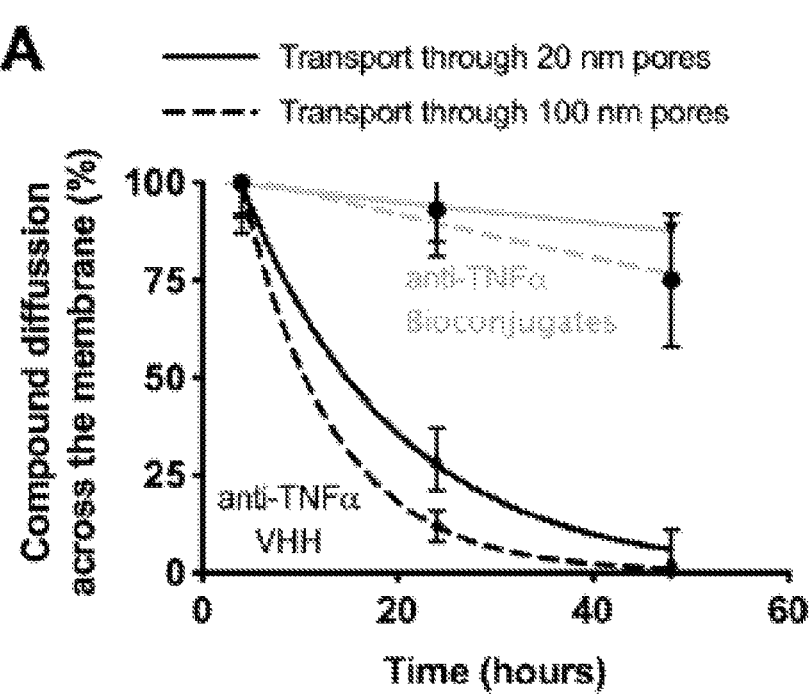
FIG. 5A shows the concentration of an anti-TNFα VHH and an anti-TNFα VHH (SEQ ID NO:7)+HyA (850 kDa) bioconjugate loaded inside a chamber comprised of fenestrated membranes at various time points over 48 hours. The average pore sizes of the membrane were either approximately 20 nm or 100 nm in diameter.
Figure 5B:
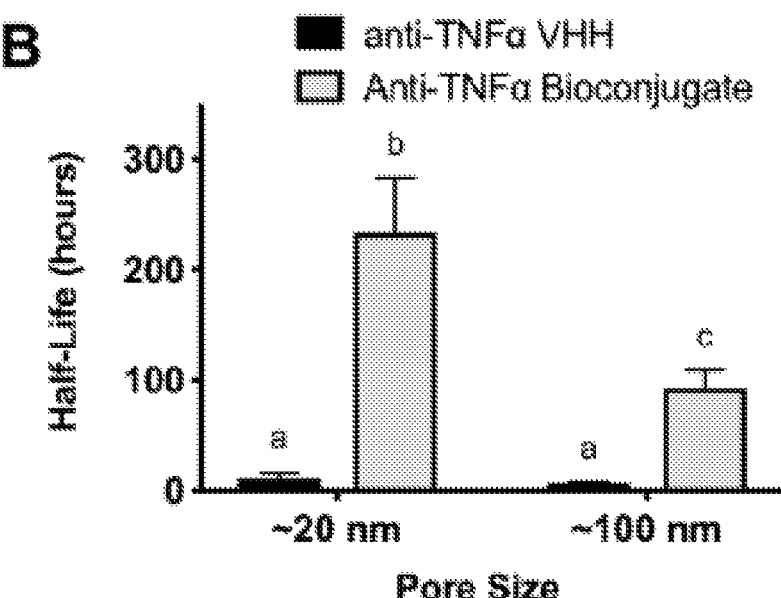
FIG. 5B shows the transport half-life of the VHH and bioconjugates as determined by an exponential decay fit ($R^2 > 0.9000$) for each of the two membrane pore sizes. The diffusion of multivalent conjugates across the membrane was substantially slower compared to the unmodified VHH antibodies (a-b, a-c, a-c: $p < 0.005$, ANOVA, n=4).

A solution of either multivalent anti-TNFα VHH bioconjugates (40 VHH:1 860 kDa HyA) or unconjugated anti-TNFα VHH was placed into chamber comprised of membranes as described above, and the concentration of VHH conjugate and unconjugated VHH that diffused across this barrier over time was measured (FIG. 5A). The multivalent conjugates diffused substantially more slowly across the membrane compare to the unconjugated protein. Further, the rate of conjugate diffusion was dependent on the pore size (FIG. 5B).

Example 5. Pharmacokinetics of Anti-inflammatory Bioconjugates

A well-known rat model was used for evaluating the clearance rate of proteins from joints to measure the IA half-life of Anti-TNF bioconjugates (Arthritis Rheum. 1999; 42(10):2094). For this assay, rats were anesthetized and the knees on their hind limbs prepared for sterile injection. Using a 30 G needle, an injection was made through synovial membrane of each knee joint, and a 40 μL injection of sterile, buffered was made into the synovial fluid. In each right knee, the injections also contained either an anti-inflammatory peptide, or an anti-inflammatory peptide at an equivalent concentration of total peptide. Generally, peptides used for this experiment have been tagged with near-infrared fluorophore (e.g., Alexa Fluor 750) using routine peptide tagging methods. At various time points for up to 10 days after the inject, the rats were imaged using an in vivo imaging system (e.g., Perkin Elmer IVIS Spectrum) to determine the intensity of fluorescence signal (e.g., average radiant efficiency) at the knees. Each left knee was used as a contralateral imaging control. Near infrared reporters can be detected in rat knees with high sensitivity using an in vivo imaging system which will enable detection down to pico-gram amounts of protein in the joint. The half-life of each treatment was determined following IA injection using established exponential decay calculations for optical in vivo imaging (Pharmaceutical research. 2013; 30(1):257). Therefore, the peptide concentration was used to estimate the intra-articular half-life of each peptide or conjugate within the joints after administration. The synovial fluid can be collected at the end of the experiment for proteomic analysis via mass spectroscopy to measure the final concentration of the peptides in the knee joint. Prior to administration, peptides were tagged with Alexa Fluor 750 near-infrared probe (ThermoFisher) following the manufacturers protocol. Briefly, peptides were mixed with Sulfo-Cy7-NHS ester at a 2:1 ratio of probe:peptide. The probe was allowed to react with the peptides for 1 hour at room temperature, and then quenched with by adding 1 part 1.5M Tris to each 10 parts of reaction solution. The peptides were purified using NAP-10 desalting columns and eluting with PBS, pH 7.0.

All groups received the same dose of total anti-TNF$\alpha$ antibody in each right knee following the IA injection protocol (40-$\mu$L of a 250 $\mu$g/mL solution: 10 $\mu$g total). This IA anti-TNF$\alpha$ antibody concentration (~80 $\mu$g/mL or 4.5 $\mu$M) is comparable to the initial IA concentrations of anti-TNF agents, such as infliximab and etanercept, when evaluated off-label to ameliorate joint inflammation in clinical studies (typically 1.5-17.5 $\mu$M).

Figure 6A:
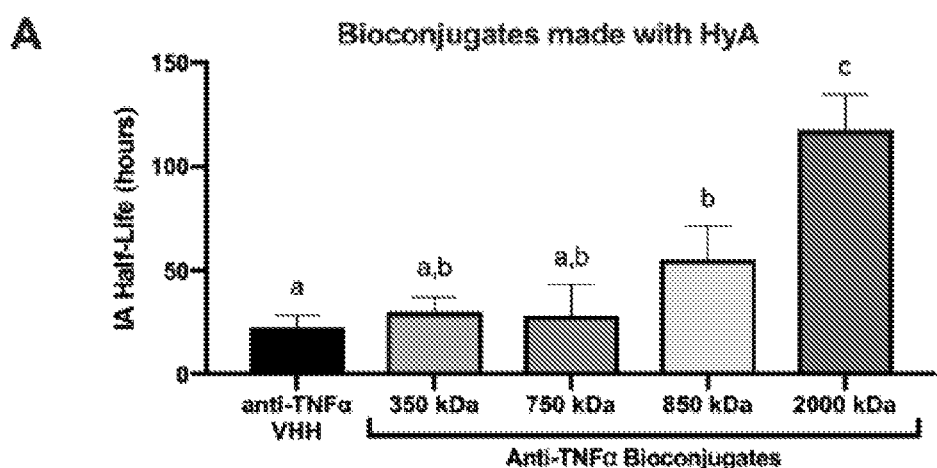
FIG. 6A shows intra-articular half-lives of anti-TNFα VHH antibodies (SEQ ID NO:7; n=4) and anti-inflammatory bioconjugates made from anti-TNFα VHH (SEQ ID NO:7) conjugated to HyA with MWs of 350 kDa (n=3), 750 kDa (n=3), 850 kDa (n=3), and 2000 kDa (n=4). The intra-articular half-lives were calculated using exponential decay fits of ROI radiant efficiency of infrared-tagged treatment peptides over 96 hours. The half-life of bioconjugates made using 850 kDa and 2000 kDa HyA were significantly longer than the unconjugated VHH (a-b: $p < 0.05$, a-c: $p < 0.0001$, b-c: $p < 0.0005$, one-way ANOVA).
Figure 6B:
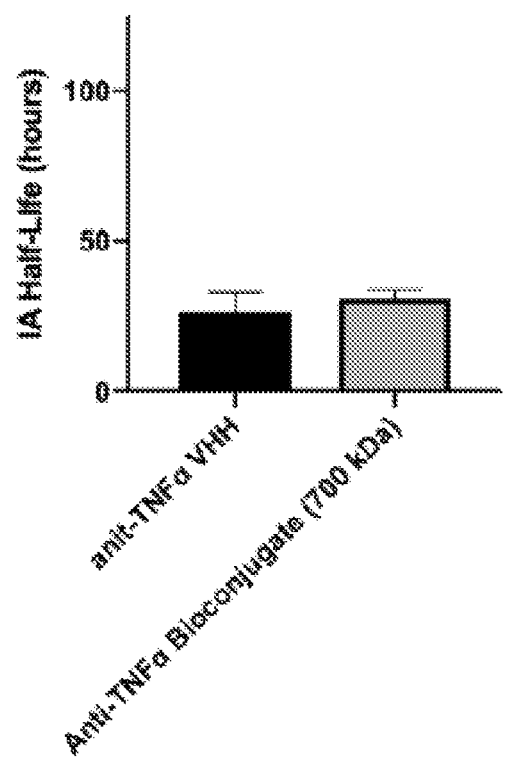
FIG. 6B shows intra-articular half-lives of anti-TNFα VHH antibodies (n=4) and anti-inflammatory bioconjugates made from anti-TNFα VHH (SEQ ID NO:7) conjugated to 700 kDa CMC (n=3). The half-life of this bioconjugate was not significantly different than that of the unconjugated VHH (p=0.32, Student's t-test).
Figure 6C:
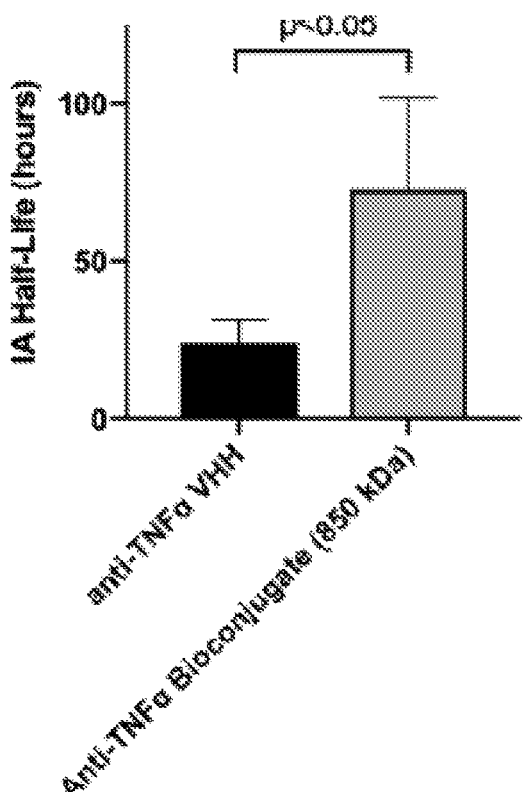
FIG. 6C shows the intra-articular half-lives of anti-TNFα VHH antibodies (n=3) and anti-inflammatory bioconjugates made from anti-TNFα VHH conjugated to 850 kDa HyA (n=3). The half-life of this bioconjugate was significantly longer than that of the unconjugated VHH (p<0.05, Student's t-test).
Figure 7:
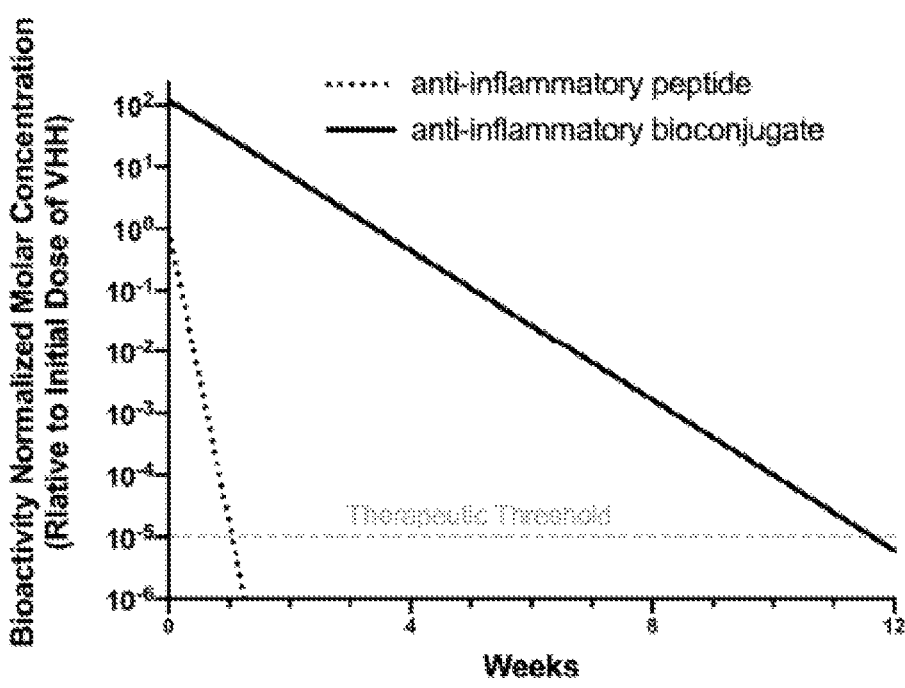
FIG. 7 shows an established pharmacology models that predict when a drug will fall below its therapeutic threshold. This model can normalize initial dose of the drugs to account of differences in the bioactivities and molecular weights of different treatments. Typically, anti-inflammatory IgG antibodies (150 kDa) require administration approximately once a week to be effective at ameliorating inflammatory joint diseases. Based on the data demonstrating an increase in potency (FIG. 4A-D) and IA half-life (FIG. 5A-B) after bioconjugation using our methods, we anticipate that a mass-equivalent dose of a bioconjugate made using a VHH antibody (15 kDa) with bioactivity equivalent to the IgGs used in previous clinical studies would require re-administration once every 11-12 weeks for an equivalent therapeutic effect.

In one set of experiments (FIG. 6A), the intra-articular half-life of anti-TNF$\alpha$ VHH antibodies (n=4) was compared to those of anti-inflammatory bioconjugates made from anti-TNF$\alpha$ VHH conjugated to HyA with MWs of 350 kDa (n=3), 750 kDa (n=3), 850 kDa (n=3), and 2000 kDa (n=4). The half-life of bioconjugates made using 850 kDa and 2000 kDa HyA were significantly longer than the unconjugated VHH. In an independent experiment (FIG. 6B), the intra-articular half-lives of anti-TNF$\alpha$ VHH antibodies (n=4) was compared to that of anti-inflammatory bioconjugates made from anti-TNF$\alpha$ VHH conjugated to 700 kDa CMC (n=3). The half-life of this bioconjugate was not significantly different than that of the unconjugated VHH. In another independent experiment, the intra-articular half-lives of anti-TNF$\alpha$ VHH antibodies (n=3) was compared to that of anti-inflammatory bioconjugates made from anti-TNF$\alpha$ VHH conjugated to 850 kDa HyA (n=3). The half-life of this bioconjugate was significantly longer than that of the unconjugated VHH.

Example 6. Pharmacological Models for the Dosing Protocol of Anti-Inflammatory Bioconjugates A model was developed to predict the required readministration frequency of anti-inflammatory peptides that is needed to maintain an effective therapeutic dose. The model is based on a model originally developed to predict the required of anti-VEGF drugs in the eye given differing local tissue half-lives and over a range of target binding affinities. The key assumption made in this model is that the drug is cleared from the target tissue following a one-phase exponential decay, and which has been demonstrated for the anti-inflammatory polymer-peptide conjugates of the present invention after intra-articular administration (see Example 3). The readministration frequency was established for an anti-inflammatory peptide to provide an effective response in a human joint (injections every 1-2 weeks) using the results of clinical research studies (PMID: 20642840, 17216015, 18415775).

Given the estimate for the intra-articular half-life of peptide drugs after intra-articular administration, the therapeutic concentration can be predicted relative to the treatment concentration. To predict the administration frequency of an equivalent dose (mg/joint) of an anti-inflammatory peptide, the difference in molarity must be accounted for given the size difference of the peptides versus the drugs used in the clinical studies (for example, the molar dose of a VHH antibody is 12 times higher than equivalent mass of an traditional IgG antibody drug). Furthermore, if the peptide has a binding affinity that is equivalent to the commercially available anti-inflammatory IgG used as a reference in the model, then the peptide-polymer conjugate will be 10 times more potent than the commercially available IgG. In the model, this is equivalent to having a starting molar concentration that is ten times higher than the dosing for the reference drug. Taking these factors together, it is possible to estimate the readministration of an anti-inflammatory drug based on the peptide-polymer conjugates.

Example 7. Clinical Protocol

Subjects suitable for treatment with a method of the present disclosure include individuals who have been diagnosed as having an inflammatory joint disease or disorder, e.g., any of the above-listed joint diseases or disorders.

Individuals suitable for treatment with a method of the present disclosure include individuals with joint pain or reduced range of joint motion due to an inflammatory joint disease or disorder. Individuals suitable for treatment with a method of the present disclosure include individuals with effluence due to an inflammatory joint disease or disorder. Individuals suitable for treatment with a method of the present disclosure include individuals with articular surface damage in a joint due to an inflammatory joint disease or disorder. Individuals suitable for treatment with a method of the present disclosure include individuals with articular wear against bone spurs, calcified cartilage, or subchondral bone lesions in a joint due to an inflammatory joint disease or disorder.

Treatment with a method of the present disclosure may be in combination with other methods of alleviating symptoms of the inflammatory joint disease or disorder, including treatment by other systemic or intra-articular drugs or by surgical intervention.

Methods suitable for measuring joint pain after treatment with a method of the present disclosure pain scoring using one or more for the following methods: Western Ontario and McMaster Universities Osteoarthritis Index (WOMAC), patient global assessment (PTGA), clinical observer global assessment (COGA), or visual analogue scale (VAS). Methods suitable for measuring the efficacy to alleviate joint pain after treatment with a method of the present disclosure pain scoring using one or more for the following methods: time until reuse of a rescue analgesic and pain assessment by VAS after a 50 foot walk. Methods suitable for measuring range of joint movement after treatment with a method of the present disclosure pain scoring include using one or more for the following instruments: goniometer or image motion tracking. Methods suitable for measuring overall patient mobility and quality of life after treatment with a method of the present disclosure pain scoring using one or more for the following methods: assessment with the Health Assessment Questionnaire (HAQ) or Short-Form 36 (SF-36) Questionnaire. Radiographic methods suitable for measuring improvements to areas of joint damage after treatment with a method of the present disclosure pain scoring using one or more for the following methods: Total Sharp Score (TSS), Joint Erosion Score, Joint Space Narrowing (JSN) score, or bone mineral quantification.

A subject displaying an abnormality on one or more of these diagnostic studies (e.g., a subject that falls outside a range that is considered normal for a healthy joint) may be treated in accordance with the present disclosure.

Example 8. Nonclinical Protocols to Assess Bioconjugate Efficacy

The efficacy of a treatment based on a method of the present disclosure to prevent osteoarthritis-induced cartilage catabolism can be assessed using a nonclinical assay as described previously. Adult (>5 months old) rats are needed for this study to enable accurate longitudinal measurements of the cartilage catabolism biomarkers, Cartilage Oligomeric Matrix Protein (COMP) and C-telopeptide of collagen type II (CTX-II). Under anesthesia, the rats will be loaded into a tibial compression system consisting of two loading platens: a bottom platen will hold the flexed knee and a top platen will hold the foot with ankle flexed to 30°. An axial force testing machine (Bose ElectroForce 3200) will apply a single 12-N compressive load at a rate of 1 mm/s. This loading method was sufficient to generate a consistent compressive injury in mice via transient anterior subluxation of the tibia relative to the distal femur.[25] The rats will then be divided into three groups randomized by weight, and each group will receive one of the following treatments: anti-inflammatory bioconjugates, unconjugated anti-inflammatory peptides, or vehicle saline.

Immediately after injury, and at the start of weeks 4, 7 and 10, anti-TNFα treatments and controls will be administered by 40-µL IA injections to the right knees. All treatment groups will receive an identical dose of total anti-TNFα antibody (250 µg/mL for a total of 10 µg total antibody per joint), yielding an IA concentration of ~80 µg/mL (~4.5 µM). 24 hours after injury, we will inject a fluorescent reporter for MMP activity (MMPSense750; 2 nmol/joint) by IA injection into both knees, MMP bioactivity will be measured in the joints on days 2, 4, and 7. At the end of weeks 1, 2, 3, 6, and 9, approximately 300 µL of blood will be collected from each rat. At the end of week 12 (day 84), all of the rats will be sacrificed, and the femurs and tibias of both hindlimbs will be collected and formalin fixed for imaging analysis. Imaging of the specimens may be performed by radiograph (Faxitron) or µCT scanning (Inveon MM CT). The specimens will then be prepared for routine decalcified histology and staining with hematoxalin/eosin and Safranin 0/Fast green to assess the extent of osteoarthritis in the joint. Histomorphometric scoring will be performed following OARSI guidelines for rat models of OA.

The efficacy of a treatment based on a method of the present disclosure to minimize joint inflammation can be assessed using a nonclinical anterior cruciate ligament (ACL) transection (ACLT) model assay as described previously. Briefly, a capsulotomy will be performed on the right knee of rats (300-400 g) to transect the ACL with a surgical scalpel, and then close the surgical sites. A sham surgery will be performed without ACLT on the left knees, which will be used as internal negative controls. 24 hours after ACLT, the rats will be divided into three groups, and each group will receive one of the following treatments: anti-inflammatory bioconjugate, unconjugated anti-inflammatory peptide, or vehicle control. At the start of weeks 4, 7 and 10, additional doses of each treatment/control will be administered by IA injection to both knees. At baseline and at the end of weeks 6 and 9, blood will be collected for inflammatory biomarker analysis and urine for metabolic markers of cartilage catabolism. At the end of week 12, a final urine sample will be collected prior to terminal blood collection for biomarker analysis. The femurs and tibiae of both hindlimbs will be harvested and imaged by radiograph (Faxitron), µCT scanning (Inveon MM CT), and MRI (BioSpec 7T). The specimens will then be prepared for routine decalcified histology and staining with hematoxalin/eosin and Safranin O/Fast green to assess the extent of osteoarthritis in the joint. Histomorphometric scoring will be performed following OARSI guidelines for rat models of OA. Serum biomarker analysis will be performed using a Luminex multiplexed ELISA array for inflammatory cytokines. This array detects 28 blood factors associated with inflammation, including those that we expect will indicate joint inflammation: IL-1β, IL-6, IL-10, and TNFα. Serum cartilage oligomeric matrix protein (COMP) and C-telopeptide of collagen type II (CTX-II) will be detected using ELISAs to quantify cartilage catabolism.

The efficacy of a treatment based on a method of the present disclosure to prevent joint inflammation and osteolysis due to intra-articular wear particles can be assessed using a nonclinical assay as described previously (PMIDs: 22275163 and 2460476) Femoral rods (15 mm×1.5 mm diameter) made from commercially pure titanium (Goodfellow USA and will be prepared for implantation by dual acid etching. Polyethylene microparticles (1.75 µm median diameter; Ceridust VP 3610) will be prepared and doped with LPS and validated by quantification as previously described.[9] The titanium rods will be implanted in the distal femurs of rats (300-400 g). One day after the implantation surgeries, weekly 40-µL intra-articular injections of LPS-doped microparticles (4.75×10⁷ particles per injection) will be performed. The rats will then be divided into three groups, and each group will receive one of the following treatments: anti-inflammatory bioconjugates, unconjugated anti-inflammatory peptides, or vehicle saline as a control. At the start of weeks 1, 4, 7 and 10, the treatments and controls will be administered by 40-µL IA injections to both knees. At baseline and at the end of weeks 6 and 9, blood will be collected for inflammatory biomarker analysis. At the end of week 12, The rats will sacrifice the rats for a terminal blood collection for biomarker analysis and to harvest the femurs and tibiae of both hindlimbs for radiographic analysis (Faxitron). The bones from one hindlimb will be fixed while the other hindlimb bones will be frozen for µCT scanning and mechanical testing. µCT scans (Scanco model 50) will be done at 3 locations perpendicular to the long axis of the implant using a 1.5 µm voxel size for assessing bone-implant contact and 10 µm voxels for assessing peri-implant trabecular and cortical bone. Mechanical pullout tests will be performed as described in detail elsewhere (Instron 8847 testing System). For static histomorphometric measurements, half of the fixed specimens will be processed for undecalcified histology by plastic embedding, grinding specimens to a mirror finish, and then surface staining with basic fuchsin and toluidine blue. The other half of the specimens will be processed for routine decalcified histology to verify the presence and distribution of microparticles at the bone-implant interface (hematoxalyn and eosin and polarized light microscopy) or osteoclast number in the peri-implant region by tartrate-resistant acidic phosphatase (TRAP) staining. Serum biomarker analysis will be performed using a Luminex multiplexed ELISA array for inflammatory cytokines. This array detects 28 blood factors associated with inflammation, including those that we expect will indicate chronic joint inflammation: IL-1, IL-6, IL-10, and TNFα.[5] We have pilot data showing how these cytokines are detectably up-regulated in the serum after intra-articular exposure to LPS-doped microparticles.

Although the foregoing invention has been described in some detail by way of illustration and Example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

Sequences (Anti-TNFa Single-Domain Heavy-chain (VHH) Antibody)

SEQ ID NO: 1

QVQLQESGGGLVQPGGSLRLSCAASGRTFSDHSGYTYTIGWFRQAPGKER

EFVARIYWSSGNTYYADSVKGRFAISRDIAKNTVDLTMNNLEPEDTAVYY

CAARDGIPTSRSVESYNYWGQGTQVTVSS (Anti-TNFa Single-Domain Heavy-chain (VHH) Antibody)

SEQ ID NO: 2

SNAQVQLQESGGGLVQPGGSLRLSCAASGRTFSDHSGYTYTIGWFRQAPGKER

EFVARIYWSSGNTYYADSVKGRFAISRDIAKNTVDLTMNNLEPEDTAVYY

CAARDGIPTSRSVESYNYWGQGTQVTVSSSPSTPPTPSPSTPPGGC

SEQ ID NO: 3

DHSGYTYTIG,

SEQ ID NO: 4

ARIYWSSGNTYYADSVKG

SEQ ID NO: 5

RDGIPT (Anti-TNFa Affibody)

SEQ ID NO: 6

SNACGGGVDN KFNKEVGWAF GEIGALPNLN ALQFRAFIIS LWDDPSQSAN         50

LLAEAKKLND AQAPK                                              65

(Anti-TNFa Single-Domain Heavy-chain (VHH) Antibody)

SEQ ID NO: 7

SNAQVQLQES GGGLVQPGGS LRLSCAASGR TFSDHSGYTY TIGWFRQAPG         50

KEREFVARIY WSSGNTYYAD SVKGRFAISR DIAKNTVDLT MNNLEPEDTA        100

VYYCAARDGI PTSRSVESYN YWGQGTQVTV SSSPSTPPTP SPSTPPGGCD        150

DDDKHHHHHH DYKDDDDK                                         168

(Anti-TNFa designed ankyrin repeat protein (DARPin))

SEQ ID NO: 8

SNADLGKKLL EVARAGQDDE VRILMANGAD VNAADHQSFT PLHLYAIFGH         50

LEIVEVLLKN GADVNASDWH GNTPLHLAAW IGHLEIVEVL LKYGADVNAT        100

DHSGSTPLHL AATLGHLEIV EVLLKYGADV NAQDKFGKTA FDISIDNGNE        150

DLAEILQKAA GGGSGGGSC                                        169

(Anti-IL-1B Single-Chain (scFv) Antibody)

SEQ ID NO: 9

SNAEIVMTQS PSTLSASVGD RVIITCQASQ SIDNWLSWYQ QKPGKAPKLL         50

IYRASTLASG VPSRFSGSGS GAEFTLTISS LQPDDFATYY CQNTGGGVSI        100

AFGQGTKLTV LGGGGSGGG GSGGGGSGGG GSEVQLVESG GGLVQPGGSL        150

RLSCTASGFS LSSAAMAWVR QAPGKGLEWV GIIYDSASTY YASWAKGRFT        200

ISRDTSKNTV YLQMNSLRAE DTAVYYCARE RAIFSGDFVL WGQGTLVTVS        250

-continued

```
SSPSTPPTPS PSTPPGGC                                          268

(Soluble interleukin receptor 2 (sILR2))
                                              SEQ ID NO: 10
HTGAARSCRF RGRHYKREFR LEGEPVALRC PQVPYWLWAS VSPRINLTWH         50

KNDSARTVPG EEETRMWAQD GALWLLPALQ EDSGTYVCTT RNASYCDKMS        100

IELRVFENTD AFLPFISYPQ ILTLSTSGVL VCPDLSEFTR DKTDVKIQWY        150

KDSLLLDKDN EKFLSVRGTT HLLVHDVALE DAGYYRCVLT FAHEGQQYNI        200

TRSIELRIKK KKEETIPVII SPLKTISASL GSRLTIPCKV FLGTGTPLTT        250

MLWWTANDTH IESAYPGGRV TEGPRQEYSE NNENYIEVPL IFDPVTREDL        300

HMDFKCVVHN TLSFQTLRTT VKESPSTPPT PSPSTPPGGC                   340

Anti-(mouse)TNFa Single-Domain Heavy-chain (VHH) Antibody
                                              SEQ ID NO: 11
SNAQVQLQDS GGGLVQAGGS LRLSCAASGG TFSSIIMAWF RQAPGKEREF         50

VGAVSWSGGT TVYADSVLGR FEISRDSARK SVYLQMNSLK PEDTAVYYCA        100

ARPYQKYNWA SASYNVWGQG TQVTVSSSPS TPPTPSPSTP PGGCDDDDKH        150

HHHHH                                                        155
```

---

What is claimed is:

1. A method of treating a disease or disorder in an articular joint, the method comprising injecting into the articular joint an effective amount of a conjugate comprising: a biocompatible polymer having a molecular weight of from about 0.8 MDa to about 3 MDa; and a plurality of peptides, wherein the peptide has a molecular weight of from about 5 kDa to about 150 kDa;

wherein the biocompatible polymer is hyaluronic acid, each peptide is covalently linked to the polymer, the peptide is covalently linked to the polymer via a sulfide bond and a linker having a molecular weight of from about 100 Da to about 500 Da, the peptide is a monoclonal IgG antibody, an IgG antibody fragment, a single-chain variable region antibody, a single-domain heavy chain antibody, an adnectin, an affibody, an anticalin, a DARPin, a Kunitz-type inhibitor, or a receptor decoy, the peptide has an amino acid sequence selected from the group consisting of SEQ ID NO:1, SEQ ID NO:2, SEQ ID NO:6, SEQ ID NO:7, SEQ ID NO:8, SEQ ID NO:9, SEQ ID NO:10 and SEQ ID NO:11, the molar ratio of the peptide to the polymer in the conjugate is at least about 5:1, and the disease or disorder is rheumatoid arthritis, wear-related osteoarthritis, age-related osteoarthritis, post-traumatic osteoarthritis, psoriatic arthritis, aseptic implant loosening, joint effusion, ankylosing spondylitis, bursitis, gout, reactive arthritis, synovitis, or avascular necrosis.

2. The method of claim 1, wherein the biocompatible polymer has a molecular weight of from about 0.8 MDa to about 2 MDa; and a plurality of peptides, wherein the peptide has a molecular weight of from about 5 kDa to about 100 kDa;

wherein the molecular weight of the polymer is from about 5 kDa to about 50 kDa per peptide.

3. The method of claim 1, wherein the biocompatible polymer has a molecular weight of from about 0.8 MDa to about 1.5 MDa.

4. The method of claim 1, wherein the biocompatible polymer has a molecular weight of about 0.9 MDa.

5. The method of claim 1, wherein the biocompatible polymer has a molecular weight of about 2 MDa.

6. The method of claim 1, wherein the peptide modulates the activity of immune cell function.

7. The method of claim 1, wherein the peptide inhibits tumor necrosis factor-α, interleukin-1β, interleukin-6, or interferon-γ.

8. The method of claim 1, wherein the peptide inhibits tumor necrosis factor-α.

9. The method of claim 1, wherein the peptide has a molecular weight of from about 5 kDa to about 30 kDa.

10. The method of claim 1, wherein the peptide has a molecular weight of from about 10 kDa to about 20 kDa.

11. The method of claim 1, wherein the peptide has an amino acid sequence according to SEQ ID NO:1:

```
                                        (SEQ ID NO: 1)
QVQLQESGGGLVQPGGSLRLSCAASGRTFSDHSGYTYTIGWFRQAPGKE

REFVARIYWSSGNTYYADSVKGRFAISRDIAKNTVDLTMNNLEPEDTAV

YYCAARDGIPTSRSVESYNYWGQGTQVTVSS.
```

12. The method of claim 1, wherein the molar ratio of the peptide to the polymer is from about 5:1 to about 400:1.

13. The method of claim 1, wherein the molar ratio of the peptide to the polymer is from about 10:1 to about 100:1.

14. The method of claim 1, wherein the molar ratio of the peptide to the polymer is from about 30:1 to about 50:1.

15. The method of claim 1, wherein the linker has a molecular weight of from about 100 Da to about 300 Da.

16. The method of claim 1, wherein the linker comprises a succinimide.

17. The method of claim 1, wherein the diffusion half-life of the conjugate is at least about 2 times longer than the diffusion half-life of the peptide.

18. The method of claim 1, wherein the diffusion half-life of the conjugate is from about 2 to about 100 times longer than the diffusion half-life of the peptide.

19. The method of claim 1, wherein the intra-articular half-life of the conjugate is at least about 20% longer than intra-articular half-life of the peptide.

20. The method of claim 1, wherein the intra-articular half-life of the conjugate is from about 20% to about 1000% longer than the intra-articular half-life of the peptide.

21. The method of claim 1, wherein the conjugate is injected into the articular joint no more than about once a month.

22. The method of claim 1, wherein the conjugate is injected into the articular joint from about once a month to once every 6 months.

23. The method of claim 1, wherein the conjugate is injected into the articular joint once every 2 months or once every 3 months.

*    *    *    *    *

SEQUENCE LISTING

<160> NUMBER OF SEQ ID NOS: 11

<210> SEQ ID NO 1
<211> LENGTH: 129
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: Anti-TNFa Single-Domain Heavy-chain (VHH)
      Antibody

<400> SEQUENCE: 1

```
Gln Val Gln Leu Gln Glu Ser Gly Gly Gly Leu Val Gln Pro Gly Gly
1               5                   10                  15

Ser Leu Arg Leu Ser Cys Ala Ala Ser Gly Arg Thr Phe Ser Asp His
            20                  25                  30

Ser Gly Tyr Thr Tyr Thr Ile Gly Trp Phe Arg Gln Ala Pro Gly Lys
        35                  40                  45

Glu Arg Glu Phe Val Ala Arg Ile Tyr Trp Ser Ser Gly Asn Thr Tyr
    50                  55                  60

Tyr Ala Asp Ser Val Lys Gly Arg Phe Ala Ile Ser Arg Asp Ile Ala
65                  70                  75                  80

Lys Asn Thr Val Asp Leu Thr Met Asn Asn Leu Glu Pro Glu Asp Thr
                85                  90                  95

Ala Val Tyr Tyr Cys Ala Ala Arg Asp Gly Ile Pro Thr Ser Arg Ser
            100                 105                 110

Val Glu Ser Tyr Asn Tyr Trp Gly Gln Gly Thr Gln Val Thr Val Ser
        115                 120                 125

Ser
```

<210> SEQ ID NO 2
<211> LENGTH: 149
<212> TYPE: PRT
<213> ORGANISM: Artificial sequence

```
<220> FEATURE:
<223> OTHER INFORMATION: Synthetic polypeptide
<220> FEATURE:
<221> NAME/KEY: misc_feature
<223> OTHER INFORMATION: Anti-TNFa Single-Domain Heavy-chain (VHH)
      Antibody

<400> SEQUENCE: 2

Ser Asn Ala Gln Val Gln Leu Gln Glu Ser Gly Gly Gly Leu Val Gln
1               5                   10                  15

Pro Gly Gly Ser Leu Arg Leu Ser Cys Ala Ala Ser Gly Arg Thr Phe
            20                  25                  30

Ser Asp His Ser Gly Tyr Thr Tyr Thr Ile Gly Trp Phe Arg Gln Ala
        35                  40                  45

Pro Gly Lys Glu Arg Glu Phe Val Ala Arg Ile Tyr Trp Ser Ser Gly
    50                  55                  60

Asn Thr Tyr Tyr Ala Asp Ser Val Lys Gly Arg Phe Ala Ile Ser Arg
65                  70                  75                  80

Asp Ile Ala Lys Asn Thr Val Asp Leu Thr Met Asn Asn Leu Glu Pro
                85                  90                  95

Glu Asp Thr Ala Val Tyr Tyr Cys Ala Ala Arg Asp Gly Ile Pro Thr
            100                 105                 110

Ser Arg Ser Val Glu Ser Tyr Asn Tyr Trp Gly Gln Gly Thr Gln Val
        115                 120                 125

Thr Val Ser Ser Ser Pro Ser Thr Pro Pro Thr Pro Ser Pro Ser Thr
    130                 135                 140

Pro Pro Gly Gly Cys
145

<210> SEQ ID NO 3
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 3

Asp His Ser Gly Tyr Thr Tyr Thr Ile Gly
1               5                   10

<210> SEQ ID NO 4
<211> LENGTH: 18
<212> TYPE: PRT
<213> ORGANISM: Artificial sequence
<220> FEATURE:
<223> OTHER INFORMATION: Synthetic polypeptide

<400> SEQUENCE: 4

Ala Arg Ile Tyr Trp Ser Ser Gly Asn Thr Tyr Tyr Ala Asp Ser Val
1               5                   10                  15

Lys Gly

<210> SEQ ID NO 5
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 5

Arg Asp Gly Ile Pro Thr
1               5
```

<210> SEQ ID NO 6
<211> LENGTH: 65
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: Anti-TNFa Affibody

<400> SEQUENCE: 6

Ser Asn Ala Cys Gly Gly Gly Val Asp Asn Lys Phe Asn Lys Glu Val
1               5                   10                  15

Gly Trp Ala Phe Gly Glu Ile Gly Ala Leu Pro Asn Leu Asn Ala Leu
                20                  25                  30

Gln Phe Arg Ala Phe Ile Ile Ser Leu Trp Asp Asp Pro Ser Gln Ser
            35                  40                  45

Ala Asn Leu Leu Ala Glu Ala Lys Lys Leu Asn Asp Ala Gln Ala Pro
        50                  55                  60

Lys
65

<210> SEQ ID NO 7
<211> LENGTH: 168
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: Anti-TNFa Single-Domain Heavy-chain (VHH)
      Antibody

<400> SEQUENCE: 7

Ser Asn Ala Gln Val Gln Leu Gln Glu Ser Gly Gly Gly Leu Val Gln
1               5                   10                  15

Pro Gly Gly Ser Leu Arg Leu Ser Cys Ala Ala Ser Gly Arg Thr Phe
                20                  25                  30

Ser Asp His Ser Gly Tyr Thr Tyr Thr Ile Gly Trp Phe Arg Gln Ala
            35                  40                  45

Pro Gly Lys Glu Arg Glu Phe Val Ala Arg Ile Tyr Trp Ser Ser Gly
        50                  55                  60

Asn Thr Tyr Tyr Ala Asp Ser Val Lys Gly Arg Phe Ala Ile Ser Arg
65                  70                  75                  80

Asp Ile Ala Lys Asn Thr Val Asp Leu Thr Met Asn Asn Leu Glu Pro
                85                  90                  95

Glu Asp Thr Ala Val Tyr Tyr Cys Ala Ala Arg Asp Gly Ile Pro Thr
                100                 105                 110

Ser Arg Ser Val Glu Ser Tyr Asn Tyr Trp Gly Gln Gly Thr Gln Val
            115                 120                 125

Thr Val Ser Ser Ser Pro Ser Thr Pro Pro Thr Pro Ser Pro Ser Thr
        130                 135                 140

Pro Pro Gly Gly Cys Asp Asp Asp Asp Lys His His His His His His
145                 150                 155                 160

Asp Tyr Lys Asp Asp Asp Asp Lys
                165

<210> SEQ ID NO 8
<211> LENGTH: 169

```
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: Anti-TNFa designed ankyrin repeat protein
      (DARPin)

<400> SEQUENCE: 8

Ser Asn Ala Asp Leu Gly Lys Lys Leu Leu Glu Val Ala Arg Ala Gly
1               5                   10                  15

Gln Asp Asp Glu Val Arg Ile Leu Met Ala Asn Gly Ala Asp Val Asn
                20                  25                  30

Ala Ala Asp His Gln Ser Phe Thr Pro Leu His Leu Tyr Ala Ile Phe
        35                  40                  45

Gly His Leu Glu Ile Val Glu Val Leu Leu Lys Asn Gly Ala Asp Val
        50                  55                  60

Asn Ala Ser Asp Trp His Gly Asn Thr Pro Leu His Leu Ala Ala Trp
65                  70                  75                  80

Ile Gly His Leu Glu Ile Val Glu Val Leu Leu Lys Tyr Gly Ala Asp
                85                  90                  95

Val Asn Ala Thr Asp His Ser Gly Ser Thr Pro Leu His Leu Ala Ala
                100                 105                 110

Thr Leu Gly His Leu Glu Ile Val Glu Val Leu Leu Lys Tyr Gly Ala
            115                 120                 125

Asp Val Asn Ala Gln Asp Lys Phe Gly Lys Thr Ala Phe Asp Ile Ser
        130                 135                 140

Ile Asp Asn Gly Asn Glu Asp Leu Ala Glu Ile Leu Gln Lys Ala Ala
145                 150                 155                 160

Gly Gly Gly Ser Gly Gly Gly Ser Cys
                165

<210> SEQ ID NO 9
<211> LENGTH: 268
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: Anti-IL-1B Single-Chain (scFv) Antibody

<400> SEQUENCE: 9

Ser Asn Ala Glu Ile Val Met Thr Gln Ser Pro Ser Thr Leu Ser Ala
1               5                   10                  15

Ser Val Gly Asp Arg Val Ile Ile Thr Cys Gln Ala Ser Gln Ser Ile
                20                  25                  30

Asp Asn Trp Leu Ser Trp Tyr Gln Gln Lys Pro Gly Lys Ala Pro Lys
        35                  40                  45

Leu Leu Ile Tyr Arg Ala Ser Thr Leu Ala Ser Gly Val Pro Ser Arg
        50                  55                  60

Phe Ser Gly Ser Gly Ser Gly Ala Glu Phe Thr Leu Thr Ile Ser Ser
65                  70                  75                  80

Leu Gln Pro Asp Asp Phe Ala Thr Tyr Tyr Cys Gln Asn Thr Gly Gly
                85                  90                  95

Gly Val Ser Ile Ala Phe Gly Gln Gly Thr Lys Leu Thr Val Leu Gly
                100                 105                 110

Gly Gly Gly Gly Ser Gly Gly Gly Gly Ser Gly Gly Gly Gly Ser Gly
```

-continued

```
          115                 120                 125
Gly Gly Gly Ser Glu Val Gln Leu Val Glu Ser Gly Gly Gly Leu Val
          130                 135                 140
Gln Pro Gly Gly Ser Leu Arg Leu Ser Cys Thr Ala Ser Gly Phe Ser
145                 150                 155                 160
Leu Ser Ser Ala Ala Met Ala Trp Val Arg Gln Ala Pro Gly Lys Gly
                    165                 170                 175
Leu Glu Trp Val Gly Ile Ile Tyr Asp Ser Ala Ser Thr Tyr Tyr Ala
                    180                 185                 190
Ser Trp Ala Lys Gly Arg Phe Thr Ile Ser Arg Asp Thr Ser Lys Asn
                    195                 200                 205
Thr Val Tyr Leu Gln Met Asn Ser Leu Arg Ala Glu Asp Thr Ala Val
          210                 215                 220
Tyr Tyr Cys Ala Arg Glu Arg Ala Ile Phe Ser Gly Asp Phe Val Leu
225                 230                 235                 240
Trp Gly Gln Gly Thr Leu Val Thr Val Ser Ser Ser Pro Ser Thr Pro
                    245                 250                 255
Pro Thr Pro Ser Pro Ser Thr Pro Pro Gly Gly Cys
                    260                 265

<210> SEQ ID NO 10
<211> LENGTH: 340
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: Soluble interleukin receptor 2 (sILR2)

<400> SEQUENCE: 10

His Thr Gly Ala Ala Arg Ser Cys Arg Phe Arg Gly Arg His Tyr Lys
1               5                   10                  15
Arg Glu Phe Arg Leu Glu Gly Glu Pro Val Ala Leu Arg Cys Pro Gln
                20                  25                  30
Val Pro Tyr Trp Leu Trp Ala Ser Val Ser Pro Arg Ile Asn Leu Thr
                35                  40                  45
Trp His Lys Asn Asp Ser Ala Arg Thr Val Pro Gly Glu Glu Glu Thr
          50                  55                  60
Arg Met Trp Ala Gln Asp Gly Ala Leu Trp Leu Leu Pro Ala Leu Gln
65                  70                  75                  80
Glu Asp Ser Gly Thr Tyr Val Cys Thr Thr Arg Asn Ala Ser Tyr Cys
                    85                  90                  95
Asp Lys Met Ser Ile Glu Leu Arg Val Phe Glu Asn Thr Asp Ala Phe
                    100                 105                 110
Leu Pro Phe Ile Ser Tyr Pro Gln Ile Leu Thr Leu Ser Thr Ser Gly
          115                 120                 125
Val Leu Val Cys Pro Asp Leu Ser Glu Phe Thr Arg Asp Lys Thr Asp
          130                 135                 140
Val Lys Ile Gln Trp Tyr Lys Asp Ser Leu Leu Leu Asp Lys Asp Asn
145                 150                 155                 160
Glu Lys Phe Leu Ser Val Arg Gly Thr Thr His Leu Leu Val His Asp
                    165                 170                 175
Val Ala Leu Glu Asp Ala Gly Tyr Tyr Arg Cys Val Leu Thr Phe Ala
                    180                 185                 190
His Glu Gly Gln Gln Tyr Asn Ile Thr Arg Ser Ile Glu Leu Arg Ile
```

```
                195                 200                 205

Lys Lys Lys Lys Glu Glu Thr Ile Pro Val Ile Ile Ser Pro Leu Lys
    210                 215                 220

Thr Ile Ser Ala Ser Leu Gly Ser Arg Leu Thr Ile Pro Cys Lys Val
225                 230                 235                 240

Phe Leu Gly Thr Gly Thr Pro Leu Thr Thr Met Leu Trp Trp Thr Ala
                245                 250                 255

Asn Asp Thr His Ile Glu Ser Ala Tyr Pro Gly Gly Arg Val Thr Glu
                260                 265                 270

Gly Pro Arg Gln Glu Tyr Ser Glu Asn Asn Glu Asn Tyr Ile Glu Val
                275                 280                 285

Pro Leu Ile Phe Asp Pro Val Thr Arg Glu Asp Leu His Met Asp Phe
    290                 295                 300

Lys Cys Val Val His Asn Thr Leu Ser Phe Gln Thr Leu Arg Thr Thr
305                 310                 315                 320

Val Lys Glu Ser Pro Ser Thr Pro Pro Thr Pro Ser Pro Ser Thr Pro
                325                 330                 335

Pro Gly Gly Cys
            340

<210> SEQ ID NO 11
<211> LENGTH: 155
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: Anti-(mouse)TNFa Single-Domain Heavy-chain
      (VHH) Antibody

<400> SEQUENCE: 11

Ser Asn Ala Gln Val Gln Leu Gln Asp Ser Gly Gly Gly Leu Val Gln
1                 5                   10                  15

Ala Gly Gly Ser Leu Arg Leu Ser Cys Ala Ala Ser Gly Gly Thr Phe
                20                  25                  30

Ser Ser Ile Ile Met Ala Trp Phe Arg Gln Ala Pro Gly Lys Glu Arg
            35                  40                  45

Glu Phe Val Gly Ala Val Ser Trp Ser Gly Gly Thr Thr Val Tyr Ala
    50                  55                  60

Asp Ser Val Leu Gly Arg Phe Glu Ile Ser Arg Asp Ser Ala Arg Lys
65                  70                  75                  80

Ser Val Tyr Leu Gln Met Asn Ser Leu Lys Pro Glu Asp Thr Ala Val
                85                  90                  95

Tyr Tyr Cys Ala Ala Arg Pro Tyr Gln Lys Tyr Asn Trp Ala Ser Ala
                100                 105                 110

Ser Tyr Asn Val Trp Gly Gln Gly Thr Gln Val Thr Val Ser Ser Ser
            115                 120                 125

Pro Ser Thr Pro Pro Thr Pro Ser Pro Ser Thr Pro Pro Gly Gly Cys
    130                 135                 140

Asp Asp Asp Asp Lys His His His His His
145                 150                 155
```